(12) United States Patent
Alshafei et al.

(10) Patent No.: US 10,934,231 B2
(45) Date of Patent: *Mar. 2, 2021

(54) MULTIPLE-STAGE CATALYST SYSTEMS AND PROCESSES FOR PROPENE PRODUCTION

(71) Applicant: Saudi Arabian Oil Company, Dhahran (SA)

(72) Inventors: Faisal H. Alshafei, Khobar (SA); Munir D. Khokhar, Khobar (SA); Sohel K. Shaikh, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/866,800

(22) Filed: Jan. 10, 2018

(65) Prior Publication Data

US 2018/0208526 A1 Jul. 26, 2018

Related U.S. Application Data

(60) Provisional application No. 62/448,476, filed on Jan. 20, 2017.

(51) Int. Cl.
*C07C 4/06* (2006.01)
*C07C 6/04* (2006.01)
(Continued)

(52) U.S. Cl.
CPC .............. *C07C 4/06* (2013.01); *B01J 8/0453* (2013.01); *B01J 21/10* (2013.01); *B01J 29/035* (2013.01);
(Continued)

(58) Field of Classification Search
CPC ..... C07C 5/22–2797; C07C 6/02; C07C 6/04; C07C 4/02–06
See application file for complete search history.

(56) References Cited

U.S. PATENT DOCUMENTS 3,442,821 A    5/1969  Lee
3,546,313 A   12/1970  Banks
(Continued)

FOREIGN PATENT DOCUMENTS

CN   102177223 A   9/2011
CN   102325742 A   1/2012
(Continued)

OTHER PUBLICATIONS

Wu et al. Investigation on acidity of zeolites bound with silica and alumina. 2002. Studies in Surface Science and Catalyisis vol. 143, pp. 217-225 (Year: 2002).*

(Continued)

*Primary Examiner* — Philip Y Louie
*Assistant Examiner* — Alyssa L Cepluch
(74) *Attorney, Agent, or Firm* — Dinsmore and Shohl LLP

(57) ABSTRACT

Processes and multiple-stage catalyst systems are disclosed for producing propene by at least partially isomerizing butene in an isomerization reaction zone having an isomerization catalyst to form an isomerization reaction product, at least partially metathesizing the isomerization reaction product in a metathesis reaction zone having a metathesis catalyst to form a metathesis reaction product, and at least partially cracking the metathesis reaction product in a cracking reaction zone having a cracking catalyst. The isomerization catalyst may be MgO, and the metathesis catalyst may be a mesoporous silica catalyst support impregnated with a metal oxide. The metathesis reaction zone may be downstream of the isomerization reaction zone, and the cracking reaction zone may be downstream of the metathesis reaction zone.

22 Claims, 7 Drawing Sheets

(51) Int. Cl.

| | | |
|---|---|---|
| C07C 5/25 | (2006.01) | |
| C07C 4/24 | (2006.01) | |
| C07C 11/06 | (2006.01) | |
| C07C 11/08 | (2006.01) | |
| B01J 21/10 | (2006.01) | |
| B01J 8/04 | (2006.01) | |
| B01J 29/40 | (2006.01) | |
| B01J 37/08 | (2006.01) | |
| B01J 29/035 | (2006.01) | |
| B01J 35/00 | (2006.01) | |
| B01J 29/03 | (2006.01) | |
| B01J 37/03 | (2006.01) | |
| B01J 37/10 | (2006.01) | |
| B01J 35/10 | (2006.01) | |
| B01J 37/06 | (2006.01) | |

(52) U.S. Cl.
CPC .......... *B01J 29/0341* (2013.01); *B01J 29/40* (2013.01); *B01J 35/002* (2013.01); *B01J 35/0006* (2013.01); *B01J 37/031* (2013.01); *B01J 37/08* (2013.01); *B01J 37/10* (2013.01); *C07C 4/24* (2013.01); *C07C 5/2512* (2013.01); *C07C 6/04* (2013.01); *C07C 11/06* (2013.01); *C07C 11/08* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/06* (2013.01); *C01P 2002/72* (2013.01); *C07C 2521/08* (2013.01); *C07C 2521/10* (2013.01); *C07C 2523/02* (2013.01); *C07C 2523/30* (2013.01); *C07C 2529/035* (2013.01); *C07C 2529/40* (2013.01); *Y02P 20/52* (2015.11)

(56) References Cited

U.S. PATENT DOCUMENTS

| | | | |
|---|---|---|---|
| 3,586,731 A | 6/1971 | Heckelsberg | |
| 3,702,886 A | 11/1972 | Argauer et al. | |
| 3,728,415 A | 4/1973 | Arganbright | |
| 4,024,201 A | 5/1977 | Takahashi | |
| 4,071,471 A | 1/1978 | Banks et al. | |
| 4,575,575 A * | 3/1986 | Drake | B01J 23/30 585/646 |
| 4,609,769 A | 9/1986 | Kukes et al. | |
| 5,026,935 A | 6/1991 | Leyshon et al. | |
| 5,026,936 A | 6/1991 | Leyshon et al. | |
| 5,191,131 A * | 3/1993 | Takahata | C07C 4/06 585/324 |
| 5,439,859 A | 8/1995 | Durante et al. | |
| 5,523,502 A | 6/1996 | Rubin | |
| 5,877,365 A | 3/1999 | Chodorge et al. | |
| 6,159,433 A | 12/2000 | Chodorge et al. | |
| 6,207,115 B1 | 3/2001 | Chodorge et al. | |
| 6,210,562 B1 | 4/2001 | Xie et al. | |
| 6,538,168 B1 | 3/2003 | Schwab et al. | |
| 6,586,649 B1 | 7/2003 | Botha et al. | |
| 6,646,172 B1 | 11/2003 | Schwab et al. | |
| 6,777,582 B2 | 8/2004 | Gartside et al. | |
| 6,977,321 B1 * | 12/2005 | Dath | C07C 4/06 585/653 |
| 7,214,841 B2 | 5/2007 | Gartside et al. | |
| 7,754,647 B2 | 7/2010 | Schubert et al. | |
| 7,754,934 B2 | 7/2010 | Tsunoda et al. | |
| 7,977,522 B2 | 7/2011 | Takai et al. | |
| 8,299,313 B2 | 10/2012 | Takai et al. | |
| 8,324,440 B2 | 12/2012 | Popp et al. | |
| 8,362,308 B2 | 1/2013 | Stephan et al. | |
| 8,440,874 B2 | 5/2013 | Ramachandran et al. | |
| 8,586,813 B2 | 11/2013 | Ramachandran et al. | |
| 8,722,568 B2 | 5/2014 | Popp et al. | |
| 9,834,497 B2 * | 12/2017 | Shaikh | C07C 6/04 |
| 9,884,794 B2 | 2/2018 | Al-Khattaf et al. | |
| 2003/0176754 A1 * | 9/2003 | Gartside | C07C 5/2512 585/643 |
| 2004/0254411 A1 | 12/2004 | Steinbrenner et al. | |
| 2005/0014981 A1 | 1/2005 | Gartside et al. | |
| 2005/0124839 A1 | 6/2005 | Gartside et al. | |
| 2006/0293548 A1 | 12/2006 | Spamer et al. | |
| 2007/0038010 A1 | 2/2007 | Xie et al. | |
| 2007/0225478 A1 | 9/2007 | Querci et al. | |
| 2008/0171655 A1 | 7/2008 | Creyghton et al. | |
| 2010/0041930 A1 * | 2/2010 | Gartside | C07C 4/06 585/314 |
| 2010/0168487 A1 | 7/2010 | Sawyer et al. | |
| 2010/0234542 A1 | 9/2010 | Blackborow et al. | |
| 2011/0021858 A1 | 1/2011 | Ramachandran et al. | |
| 2011/0152595 A1 | 6/2011 | Takai et al. | |
| 2011/0196185 A1 | 8/2011 | Krawczyk et al. | |
| 2012/0108864 A1 | 5/2012 | Gartside et al. | |
| 2012/0264990 A1 * | 10/2012 | Nicholas | B01J 37/18 585/646 |
| 2012/0283090 A1 | 11/2012 | Popp et al. | |
| 2012/0289617 A1 * | 11/2012 | Wang | B01J 31/20 521/33 |
| 2013/0085311 A1 | 4/2013 | Youn et al. | |
| 2013/0165701 A1 | 6/2013 | Zhou et al. | |
| 2013/0245348 A1 | 9/2013 | Vermeiren et al. | |
| 2014/0148629 A1 | 5/2014 | van Hal et al. | |
| 2015/0141720 A1 * | 5/2015 | Ramachandran | B01J 35/1019 585/312 |
| 2015/0141721 A1 * | 5/2015 | Choi | B01J 8/0453 585/315 |
| 2016/0130197 A1 | 5/2016 | Al-Khattaf et al. | |
| 2016/0237006 A1 * | 8/2016 | Stoyanova | B01J 35/1019 |
| 2017/0001925 A1 | 1/2017 | Abudawoud et al. | |
| 2017/0001926 A1 * | 1/2017 | Shaikh | C07C 6/04 |
| 2017/0001927 A1 | 1/2017 | Al-Khattaf et al. | |
| 2018/0057425 A1 * | 3/2018 | Shaikh | C07C 6/04 |
| 2018/0142167 A1 | 5/2018 | Al-Ghamdi et al. | |
| 2018/0155256 A1 * | 6/2018 | Al-Khattaf | C07C 6/04 |
| 2018/0208526 A1 | 7/2018 | Alshafei et al. | |
| 2018/0230071 A1 | 8/2018 | Bonduelle et al. | |

FOREIGN PATENT DOCUMENTS

| | | | |
|---|---|---|---|
| CN | 101531558 B | 4/2013 | |
| CN | 104370676 A * | 2/2015 | ............ C07C 11/04 |
| CN | 104370676 A | 2/2015 | |
| DE | 10013253 A1 | 9/2001 | |
| EP | 304515 B1 | 12/1991 | |
| EP | 0920911 A1 | 6/1999 | |
| EP | 2151424 A1 | 2/2010 | |
| GB | 1205677 A | 9/1970 | |
| JP | 2003500190 A | 1/2003 | |
| JP | 2012500304 A | 1/2012 | |
| KR | 20110056510 A | 5/2011 | |
| KR | 20130059594 A | 6/2013 | |
| NL | 8403050 A | 5/1986 | |
| RU | 2370314 C1 | 10/2009 | |
| WO | 9929805 A1 | 6/1999 | |
| WO | 00/71255 A1 | 11/2000 | |
| WO | 2006089957 A1 | 8/2006 | |
| WO | 2009015118 A2 | 1/2009 | |
| WO | 2009117128 A1 | 9/2009 | |
| WO | 2010019595 A2 | 2/2010 | |
| WO | 2008136280 A1 | 7/2010 | |
| WO | 2011136983 A1 | 11/2011 | |
| WO | 2015055594 A1 | 4/2015 | |
| WO | 2017-003812 A1 | 1/2017 | |
| WO | 2017/003817 A1 | 1/2017 | |
| WO | 2017/003821 A1 | 1/2017 | |
| WO | 2018088815 A1 | 5/2018 | |

OTHER PUBLICATIONS

Sigma Aldrich Silica gel Davisil 646. Jun. 8, 2018. (Year: 2018).*
Machine translation CN 104370676. Feb. 25, 2015. (Year: 2015).*
U.S. Non-Final Office Action dated Jan. 9, 2018 pertaining to U.S. Appl. No. 15/398,196.

(56) References Cited

OTHER PUBLICATIONS

Arudra et al., "Silicalite-1 as Efficient Catalyst for Production of Propene from 1-Butene", ACS Catalysis, 2014, 4205-4212, 4, American Chemical Society.
Awayssa et al., "Modified HZSM-5 as FCC Additive for Enhancing Light Olefins Yield from Catalytic Cracking of VGO", Applied Catalysis A: General, 2014, 172-183, 477.
Balcar, et al., Mesoporous molecular sieves as advanced supports for olefin metathesis catalysts, Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., Highly Active Doped Mesoporous KIT-6 Catalysts for Metathesis of 1-Butene and Ethene to Propene: The Influence of Neighboring Environment of W Species, The Journal of Physical Chemistry, ACS Publication, 2013 American Chemical Society, pp. 26385-26395, USA.
Daniell et al., Enhanced Surface Acidity in Mixed Alumina-Silicas: A Low-Temperature FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., Performance of Nano Crystalline H-ZSM-5 As Additive in FCC Catalyst: A Review, International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Office Action pertaining to U.S. Appl. No. 15/190,950 dated Sep. 27, 2017.
Office Action pertaining to U.S. Appl. No. 15/190,964 dated Nov. 2, 2017.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2C12(CHCMe3)(OR2) and W(OAr)2Cl(CHCMe3)(CH2CMe3)(OR2)", Journal of Molecular Catalysis, 1986, 36, 13-29.

Ruihua Gao, et al., High-activity, single-site mesoporous WO3-MCF materials for the catalytic epoxidation of cycloocta-1,5-diene with aqueous hydrogen peroxide, Journal of Catalysis, 256, 2008, pp. 259-267, China.
Wang et al., Synthesis and Structure of Silicalite-1/SBA-15 Composites Prepared by Carbon Templating and Crystallization, Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018 pertaining to International PCT Application No. PCT/US2016/039012.
International Preliminary Report on Patentability dated Jan. 11, 2018 pertaining to International PCT Application No. PCT/US2016/038967.
Non-Final Office Action pertaing to U.S. Appl. No. 15/398,196 dated Jan. 9, 2018.
Puriwat, et al., "Elucidation of the basicity dependence of 1-butene isomerization on MgO/Mg(OH)s catalysts", Catalysis Communications, 2010, pp. 80-85.
International Search Report and Written opinion dated Mar. 28, 2018, pertaining to International Application No. PCT/US2018/013945, filed Jan. 17, 2018, 9 pages.
Korean Office Action pertaining to Korea Application No. 10-2018-7003238 dated May 14, 2018 (English Translation).
U.S. Office Action dated Apr. 20, 2018 pertaining to U.S. Appl. No. 15/859,794, filed Jan. 2, 2018.
International Search Report and Written Opinion dated Apr. 24, 2018 pertaining to International Application No. PCT/US2018/014131, filed Jan. 18, 2018.
Notice of Allowance dated Apr. 24, 2018 pertaining to U.S. Appl. No. 15/190,964, filed Jun. 23, 2016.
Election/Restriction Requirement dated May 21, 2018, pertaining to U.S. Appl. No. 15/866,772, filed Jan. 10, 2018.
Examination Report pertaining to GCC Application No. 2016/31672 dated Sep. 13, 2018.
Notice of Allowance dated Mar. 5, 2019 pertaining to U.S. Appl. No. 15/866,772, filed Jan. 10, 2018.
Office Action dated Apr. 29, 2019 pertaining to U.S. Appl. No. 16/039,983, filed Jul. 19, 2018, 36 pgs.
Yuan Guimei et al., Machine translation of CN 104370676, Feb. 2015.
Office Action dated May 2, 2019 pertaining to U.S. Appl. No. 15/859,794, filed Jan. 2, 2018, 30 pgs.
Office Action dated May 2, 2019 pertaining to U.S. Appl. No. 16/156,634, filed Oct. 10, 2018, 32 pgs.
Office Action dated Apr. 5, 2019 pertaining to U.S. Appl. No. 15/873,421, filed Jan. 17, 2018, 49 pgs.
Office Action dated Aug. 28, 2018 pertaining to U.S. Appl. No. 15/866,772, filed Jan. 10, 2018, 41 pgs.
Harmse et al., "On the Product Formation in 1-Butene Mehathesis over Supported Tungsten Catalysts", Catal. Lett., 137; p. 123-131, 2010.
Shaikh, et al., "Self-Methathesis of Butenes to Propylene", Catalysis in Petroleum Refining & Petrochemicals, pp. 1-6, Dec. 7-8, 2015.
Debecker, et al., "Preparation of MoO3/SiO2—Al2O3 methathesis catalysts via wet impregnation with different Mo precursors", Journal of Molecular Catalysis A: Chemical, 340, pp. 65-76, 2011.
Wu, et al., "Investigation on acidity of zeolites bound with silica and alumina", Studies in Surface Science and Catalysis, 143, pp. 217-225, 2002.
Office Action dated Apr. 4, 2017 pertaining to U.S. Appl. No. 15/190,981, filed Jun. 23, 2016, 14 pgs.
Examination Report for Application No. GC 2018/34631 dated Aug. 22, 2019.
European Search Report for Application No. 19163840.2 dated Aug. 2, 2019.

(56) References Cited

OTHER PUBLICATIONS

Chinese Office Action for Application No. 201811179717.1 dated Jun. 13, 2019.
European Search Report for Application No. 16738274.6 dated Aug. 2, 2019.
Decision of Rejection pertaining to Japanese Application No. 2017-567370 dated Sep. 4, 2019.
Office Action dated Jun. 18, 2019 pertaining to Korean Patent Application No. 10-2018-7003251.
Office Action dated Mar. 30, 2019 pertaining to Japanese Patent Application No. 2017-567370.
Notice of Allowance and Fee(s) due dated Oct. 18, 2019 pertaining to U.S. Appl. No. 16/039,983, filed Jul. 19, 2018, 29 pgs.
Machine translation claims of CN 102177223 A, Sep. 2011.
Machine translation description CN 102177223 A, Sep. 2011.
Notice of Allowance and Fee(s) Due dated May 15, 2019 pertaining to U.S. Appl. No. 16/156,616, filed Oct. 10, 2018, 35 pgs.
Notice of Allowance and Fee(s) Due dated Aug. 29, 2019 pertaining to U.S. Appl. No. 15/859,794, filed Jan. 2, 2018, 22 pgs.
Notice of Allowance and Fee(s) Due dated Sep. 26, 2019 pertaining to U.S. Appl. No. 15/873,421, filed Jan. 17, 2018, 30 pgs.
Office Action pertaining to Korean Application No. 10-2019-7005618 dated Feb. 25, 2020.
Office Action pertaining to Application No. CN201680039097.4 dated Mar. 4, 2020, 7 pgs.
Search Report pertaining to Application No. CN201680039097.4 dated Feb. 25, 2020.
Office Action pertaining to application No. CN201811179717.1 dated Mar. 17, 2020, 7 pgs.
Examination Report pertaining to GCC Application No. 2016/31673 dated Apr. 7, 2020.
Office Action dated Dec. 17, 2019 pertaining to Chinese Patent Application No. 201680038823.0.
Office Action dated Oct. 25, 2019 pertaining to Japanese Patent Application No. 2017-568232.
Office Action dated Jan. 5, 2020 pertaining to GCC Patent Application No. 2016-37609.
International Search Report and Written Opinion pertaining to Application No. PCT/US2019/054378 dated Jan. 13, 2020.
International Search Report and Written Opinion pertaining to Application No. PCT/US2019/054377 dated Jan. 13, 2020.
Office Action pertaining to U.S. Appl. No. 16/390,523 dated Jan. 17, 2020.
Bortnovsky et al., "Cracking of pentenes to C2-C4 light olefins over zeolites and zeotypes Role of topology and acid site strength and concentration", Applied Catalysis A: General 287, pp. 203-213, 2005.
Debecker et al., "Aerosol route to nanostructured WO3—SiO2—Al2O3 methathesis catalysts: Toward higer propene yield", Applied Catalysis A: General 470, pp. 458-466, 2014.
Office Action dated Nov. 20, 2019 pertaining to U.S. Appl. No. 16/156,634, filed Oct. 10, 2018, 37 pgs.
Search Report and Written Opinion pertaining to Singapore Application No. 10201913486W dated Jul. 21, 2020.
U.S. Office Action dated Aug. 21, 2020 pertaining to U.S. Appl. No. 16/712,280, filed Dec. 12, 2019, 67 pgs.
U.S. Office Action dated Sep. 15, 2020 pertaining to U.S. Appl. No. 16/156,634, filed Oct. 10, 2018, 38 pgs.
U.S. Office Action dated Sep. 16, 2020 pertaining to U.S. Appl. No. 16/522,142, filed Jul. 25, 2019, 72 pgs.
Office Action dated May 27, 2020 pertaining to U.S. Appl. No. 16/156,616, filed Oct. 10, 2018, 31 pgs.
Office Action dated Jul. 14, 2020 pertaining to U.S. Appl. No. 16/390,523, filed Apr. 22, 2019, 42 pgs.

\* cited by examiner

MULTIPLE-STAGE CATALYST SYSTEMS AND PROCESSES FOR PROPENE PRODUCTION

CROSS REFERENCE TO RELATED APPLICATIONS

This application claims the benefit of U.S. Provisional Application Ser. No. 62/448,476 filed Jan. 20, 2017.

TECHNICAL FIELD

Embodiments of the present disclosure is generally related to catalytic propene production and, more specifically, to converting butene to propene using a multiple-stage catalyst system.

BACKGROUND

In recent years, there has been a dramatic increase in the demand for propene to feed the growing markets for polypropylene, propylene oxide, and acrylic acid. Currently, most of the propene produced worldwide is a by-product from steam cracking units which primarily produce ethylene, or a by-product from fluid catalytic cracking (FCC) units, which primarily produce gasoline. These processes cannot respond adequately to a rapid increase in propene demand.

Other propene production processes contribute a relatively small amount of total propene production. Among these processes are propane dehydrogenation (PDH), metathesis reactions requiring both ethylene and butene, high severity FCC, olefins cracking, and methanol to olefins (MTO) processes. However, propene demand has exceeded ethylene and gasoline/distillate demand, and propene supply has not kept pace with this increase in propene demand.

SUMMARY

Accordingly, an ongoing need exists for improved processes for the selective production of propene. Embodiments of the present disclosure are directed to propene production from butenes by a multiple-stage catalyst system.

According to one or more embodiments, a process for producing propene may comprise at least partially isomerizing butene with an isomerization catalyst to form an isomerization reaction product. The isomerization catalyst may comprise magnesium oxide (MgO). The process may comprise at least partially metathesizing the isomerization reaction product with a metathesis catalyst to form a metathesis reaction product. The metathesis catalyst may comprise a mesoporous silica catalyst support impregnated with metal oxide. The process may also comprise at least partially cracking the metathesis reaction with a cracking catalyst to form a cracking reaction product. The cracking reaction product may comprise propene.

According to another embodiment, a process for producing propene may comprise introducing a stream comprising butene to an isomerization reaction zone comprising an isomerization catalyst. The isomerization catalyst may comprise magnesium oxide (MgO). The process may comprise at least partially isomerizing the stream comprising butene in the isomerization reaction zone to form an isomerization reaction product stream and passing the isomerization reaction product stream to a metathesis reaction zone that comprises a metathesis catalyst. The metathesis catalyst may comprise a mesoporous silica catalyst support impregnated with metal oxide. The process may further comprise at least partially metathesizing the isomerization reaction product stream with the metathesis catalyst to form a metathesis reaction product stream, passing the metathesis reaction product stream to a cracking reaction zone that comprises a cracking catalyst, and at least partially cracking the metathesis reaction product stream with the cracking catalyst to form a cracking reaction product stream that comprises propene.

According to yet another embodiment, a multiple-stage catalyst system for producing propene may comprise an isomerization reaction zone, a metathesis reaction zone downstream of the isomerization reaction zone, and a cracking reaction zone downstream of the metathesis reaction zone. The isomerization reaction zone may comprise magnesium oxide (MgO), the metathesis reaction zone may comprise a mesoporous silica catalyst support impregnated with metal oxide, and the cracking reaction zone may comprise a zeolite catalyst. The zeolite catalyst may crack the metathesis product stream to form a cracking product stream that comprises propene.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
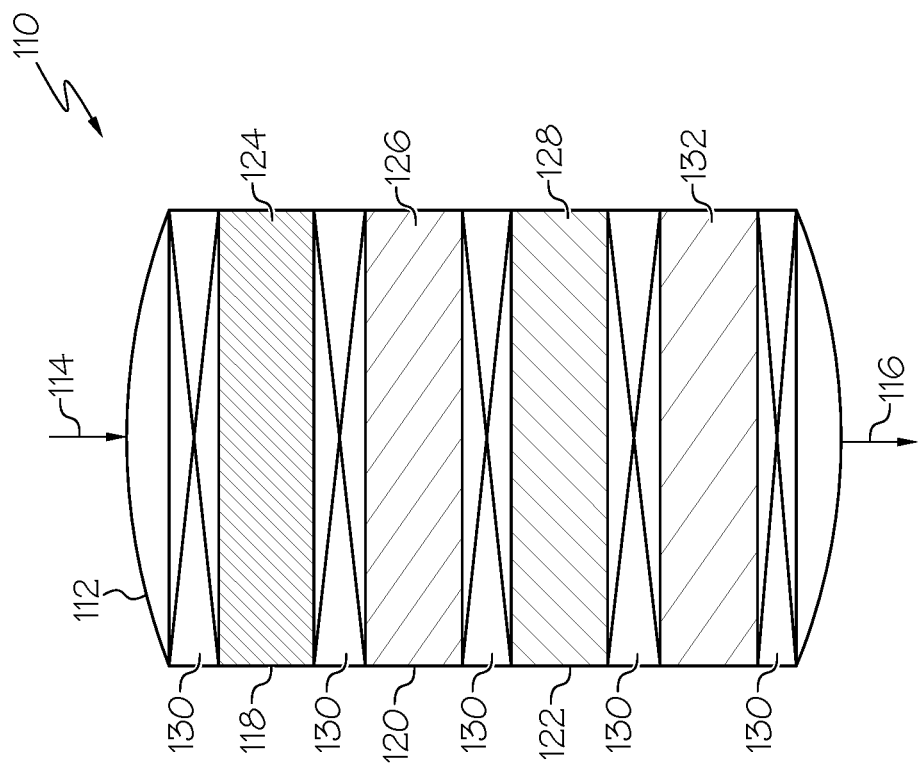
FIG. 1 schematically depicts a fixed bed continuous flow reactor including an isomerization reaction zone, a metathesis reaction zone, and a cracking reaction zone, according to one or more embodiments of the present disclosure.

Embodiments of the present disclosure are directed to systems and methods for converting a hydrocarbon stream containing butene to a stream comprising propene by catalyzed isomerization, catalyzed metathesis, and catalyzed cracking. Specifically, the present embodiments are related to a multiple-stage (for example, three-stage) catalyst systems containing isomerization, metathesis, and cracking catalysts for propene production from a feed stream containing butene. While a three-stage catalyst system with 3 catalysts is used throughout this disclosure for simplicity and clarity, it may be appreciated that the multiple-stage catalyst system may include more than 3 catalysts, such as 4 catalysts, 5 catalysts, 6 catalysts, or even more catalysts. In one or more embodiments, the isomerization catalyst is followed by the metathesis catalyst, and the metathesis catalyst is followed by the cracking catalyst (that is, in series), which may provide an improved yield of propene, and optionally an improved combined yield of propene and ethylene as compared to other metathesis reaction systems. In one or more other embodiments, one or more of the isomerization catalyst, metathesis catalyst, and cracking catalysts may be mixed together such that one or more of the isomerization reaction, metathesis reaction, and cracking reaction may occur in the same fixed catalyst bed, as will be described in further detail subsequently in this disclosure. The hydrocarbon stream which is introduced to the catalysts may be any stream comprising butene, which may include 1-butene, cis-2-butene, trans-2-butene, or combinations of these isomers. In one or more embodiments, the hydrocarbon stream comprising butene may be a raffinate stream created by a naphtha cracking process.

As used in this disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Example reactors include packed bed reactors, such as fixed bed reactors, and fluidized bed reactors. A reaction system may include one or more "reaction zones." As used in this disclosure, a "reaction zone" refers to an area where a particular reaction takes place. For example, a packed bed reactor with multiple catalyst beds may have multiple reaction zones, where each reaction zone is defined by the area of each catalyst bed. In another non-limiting example, a multi-stage catalyst reaction system may include multiple reactors, and each reactor may define a separate "reaction zone."

In one or more embodiments of a multi-catalyst reaction system, a catalyst in each reaction zone may have a relatively small amount of different types of catalysts from the other reaction zones. For example, the reaction zone may have less than 10 weight percent (wt. %) of the catalyst from another reaction zone, or even less than 5 wt. % of the catalysts from another reaction zone. In one or more embodiments, a reaction zone may comprise a mixture of one or more catalysts.

As shown in Chemical Formula 1, provided subsequently in the present disclosure, isomerization of 2-butenes (which may include isomers cis-2-butene, trans-2-butene, or both) to 1-butene, and vice versa, is an equilibrium reaction as denoted by the bi-directional arrows with single heads. The isomerization may be achieved with the isomerization catalyst. An "isomerization catalyst," as used in this disclosure, is a catalyst that promotes isomerization of alkenes, including, for example, isomerization of 2-butenes to 1-butene. Cross-metathesis may be achieved as shown in Chemical Formula 2, provided subsequently in the present disclosure, with the metathesis catalyst. As used in this disclosure, "cross-metathesis" refers to an organic reaction that involves the redistribution of fragments of alkenes by the scission and regeneration of carbon-carbon double bonds. In the case of 2-butenes and 1-butene, the redistribution of these carbon-carbon double bonds through metathesis produces propene and $C_5$-$C_6$ olefins. A "metathesis catalyst," as used in this disclosure, refers to a catalyst that promotes the metathesis reaction of alkenes to form other alkenes. The metathesis catalyst may also isomerize 2-butenes to 1-butene through a "self-metathesis" reaction mechanism. Further, as shown in the following Chemical Formula 3, "cracking" refers to the catalytic conversion of $C_4$-$C_6$ alkenes to propene and other alkanes, alkenes, or alkanes and alkenes, for example, $C_1$-$C_2$ alkenes.

Chemical Formula 1: 2-Butene Isomerization

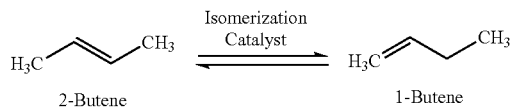

Chemical Formula 2: Cross-Metathesis

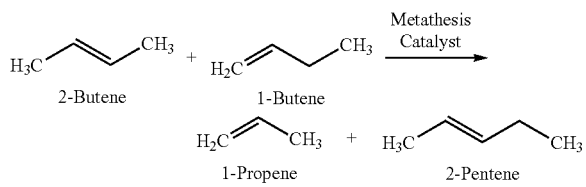

Chemical Formula 3: Cracking

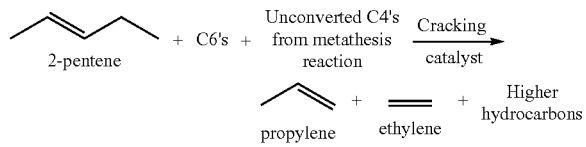

Referring to Chemical Formulas 1-3, the isomerization, metathesis, and cracking reactions are not limited to these reactants and products; however, Chemical Formulas 1-3 provide a simplified illustration of the reaction methodology. As shown in Chemical Formulas 1 and 2, metathesis reactions may take place between two alkenes. The groups bonded to the carbon atoms of the carbon-carbon double bond may be exchanged between the molecules to produce two new alkenes with the exchanged groups. The specific catalyst that is selected for the olefin metathesis reaction may generally determine whether a cis-isomer or trans-isomer is formed, as the formation of a cis- or trans-isomer may be a function at least partially of the coordination of the olefin molecules with the catalyst, as may be the steric influences of the substituents on the carbon-carbon double bond of the newly formed molecule.

In operation, a product stream comprising propene may be produced from a stream containing butene by isomerization, metathesis conversion, and cracking by contacting the stream containing butene with the multiple-stage catalyst system. The stream containing butene may include 2-butene, which may include isomers cis-2-butene, trans-2-butene, or both. The stream containing butene may optionally include 1-butene. The present disclosure focuses, in some embodiments, on streams containing 2-butene, 1-butene, or both; however, it is known that other $C_1$-$C_6$ components may also be present in the stream containing butene. Trace amount of isobutene or higher amount of inert gases like n-butane may not harm the reaction or the amount of side products formed during the reactions are so negligible they do not affect the overall yield of total propene.

Referring to FIG. 1, an embodiment of the multiple-stage catalyst system for producing propene from a stream containing butene is illustrated, the multiple-stage catalyst system being designated by reference number 110. The multiple-stage catalyst system 110 may include an isomerization reaction zone 118, a metathesis reaction zone 120, and a cracking reaction zone 122. The metathesis reaction zone 120 may be positioned downstream of the isomerization reaction zone 118, and the cracking reaction zone 122 may be positioned downstream of the metathesis reaction zone 120. In one or more embodiments, the multiple-stage catalyst system 110 may include a reactor 112. As depicted in FIG. 1, an inlet stream 114 is introduced to the reactor 112, and an outlet stream 116 passes out of the reactor 112. In some embodiments, the multiple-stage catalyst system 110 may comprise the isomerization reaction zone 118, the metathesis reaction zone 120, and the cracking reaction zone 122 disposed within the reactor 112. Thus, reactant contents pass into the isomerization reaction zone 118 via the inlet stream 114, through the isomerization reaction zone 118, the metathesis reaction zone 120, and the cracking reaction zone 122, and are passed out of the cracking zone as the outlet stream 116.

Figure 8:
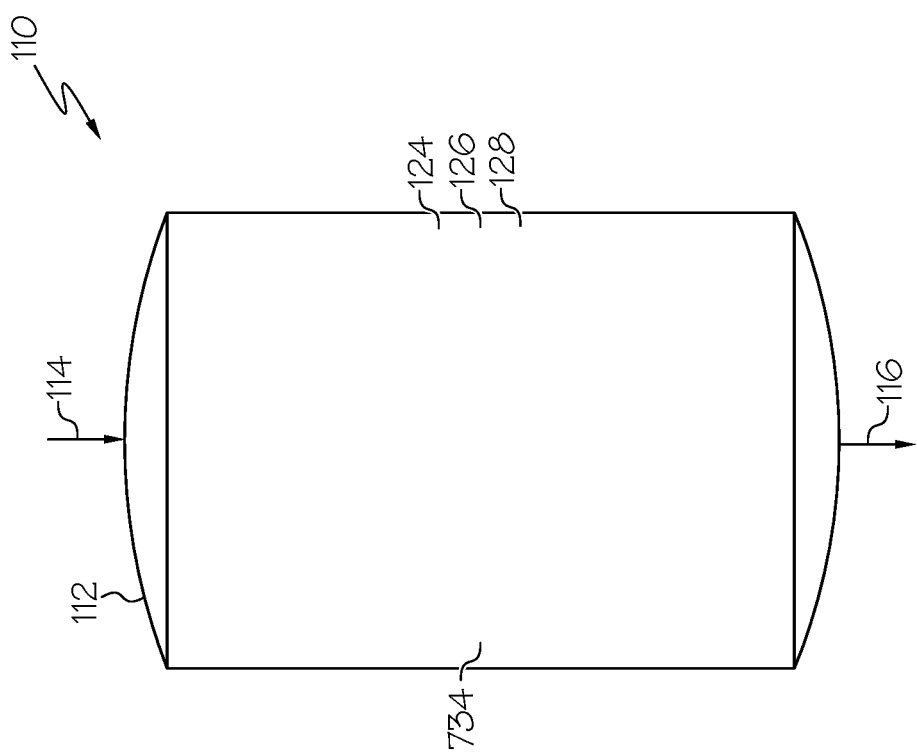
FIG. 8 schematically depicts another fixed bed continuous flow reactor including an isomerization catalyst, a metathesis catalyst, and a cracking catalyst, according to one or more embodiments of the present disclosure.

While not depicted in FIG. 1, it should be understood that in other embodiments, each reaction zone (that is, the isomerization reaction zone 118, the metathesis reaction zone 120, and the cracking reaction zone 122) may be disposed in its own reactor, arranged in series. In such an embodiment, three reactors may be arranged in series, where the effluent of the upstream reactor enters the downstream reactor in an inlet stream. In other embodiments, one or more of the isomerization reaction zone 118, metathesis reaction zone 120, or cracking reaction zone 122 may include an admixture of two or more of the isomerization catalyst 124, metathesis catalyst 126, or cracking catalyst 128. For example, as schematically depicted in FIG. 8, in embodiments, all three of the isomerization catalyst 124, metathesis catalyst 126, and cracking catalyst 128 may be admixed in a single reaction zone 734 within a single reactor 112. Alternatively, the multiple-stage catalyst system 110 may comprise an upstream reactor comprising the isomerization catalyst 124, such as MgO, which may be operated at a slightly reduced temperature, and a downstream reactor comprising the metathesis catalyst and the cracking catalyst, which may be operated at a slightly greater temperature. In another example, the upstream reactor may include the isomerization catalyst 124 and metathesis catalyst 126 and the downstream reactor may include a second amount of the metathesis catalyst 126 and the cracking catalyst. It is understood that many reactor configurations and catalyst layering methods may be employed in the multiple-stage catalyst systems 110 described in this disclosure.

As described previously in this disclosure, 2-butene (including isomers cis-2-butene, trans-2-butene, or both) may be present in the inlet stream 114 stream, and the inlet stream 114 may contain 2-butene in an amount from 10 wt. % to 70 wt. %, from 10 wt. % to 60 wt. %, from 10 wt. % to 50 wt. %, from 10 wt. % to 40 wt. %, from 20 wt. % to 70 wt. %, from 20 wt. % to 60 wt. %, from 20 wt. % to 50 wt. %, from 20 wt. % to 40 wt. %, from 30 wt. % to 70 wt. %, from 30 wt. % to 60 wt. %, from 30 wt. % to 50 wt. %, from 30 wt. % to 40 wt. %, or from 10 wt. % to 30 wt. %. In some embodiments, the inlet stream 114 may include 1-butene in an amount from 5 wt. % to 60 wt. %, from 5 wt. % to 50 wt. %, from 5 wt. % to 40 wt. %, from 10 wt. % to 60 w. %, from 10 wt. % to 50 wt. %, from 10 wt. % to 40 wt. %, from 15 wt. % to 60 wt. %, from 15 wt. % to 50 wt. %, from 15 wt. % to 40 wt. %, from 5 wt. % to 20 wt. %, or from 40 wt. % to 60 wt. %. In some embodiments, the inlet stream 114 may also include n-butane in an amount from 5 wt. % to 30 wt. %, from 10 wt. % to 30 wt. %, from 15 wt. % to 30 wt. %, from 5 wt. % to 25 wt. %, from 10 wt. % to 25 wt. %, from 15 wt. % to 25 wt. %, from 5 wt. % to 15 wt. %, or from 25 wt. % to 30 wt. %. In one or more embodiments, the inlet stream 114 may be a raffinate-2 stream that includes from 20 wt. % to 60 wt. % of cis- or trans-2-butene, or both, from 10 wt. % to 60 wt. % of 1-butene, and from 15 wt. % to 25 wt. % n-butane. In one or more embodiments, the inlet stream 114 may be a raffinate-3 stream that may include from 30 wt. % to 70 wt. % of cis- or trans-2-butene and from 10 wt. % to 30 wt. % of n-butane. In one or more embodiments, the inlet stream 114 may be a raffinate-1 stream that may include from 10 wt. % to 30 wt. % of cis- or trans-2-butene, or both, from 25 wt. % to 50 wt. % of 1-butene, and from 20 wt. % to 50 wt. % isobutene. In one or more embodiments, the inlet stream 114 containing butene may be substantially free of ethylene. As used in this disclosure, the term "substantially free" of a component means less than 1 wt. % of that component in a particular portion of a catalyst, stream, or reaction zone. As an example, the inlet stream 114, which may be substantially free of ethylene, may have less than 1 wt. % of ethylene. In one or more embodiments, the inlet stream 114 containing butene may be substantially free of isobutene. In one or more embodiments, the inlet stream 114 containing butene may have less than 0.1 wt. % of isobutene. In one or more embodiments, the inlet stream 114 containing butene may be a raffinate-1 stream having from 20 wt. % to 50 wt. percent isobutene.

The isomerization reaction zone 118 of the multiple-stage catalyst system 110 may include an isomerization catalyst 124. The isomerization catalyst 124 may promote equilibration of the isomerization reaction of 2-butene in the inlet stream 114 to 1-butene, and vice versa. For an inlet stream 114 having a greater concentration of 2-butene compared to 1-butene, the isomerization catalyst 124 may isomerize at least a portion of the 2-butene to 1-butene. The isomerization reaction zone 118 may produce an isomerization reaction product that may include 2-butene (cis-, trans-, or both) and 1-butene. The isomerization catalyst 124 may also operate to maintain equilibrium concentrations between 1-butene and 2-butene in the isomerization reaction product. In one or more embodiments, the isomerization catalyst 124 may be magnesium oxide (MgO).

The metathesis reaction zone 120 may include a metathesis catalyst 126. In the metathesis reaction zone 120, the metathesis catalyst 126 may convert the 1-butene and 2-butene in the isomerization reaction product, which is produced in the isomerization reaction zone 118, to propene and other alkenes through cross-metathesis. The metathesis reaction zone 120 may produce a metathesis reaction product that may include propene and other alkanes and alkenes, such as propene and other $C_5+$ olefins, for example. The metathesis reaction product may also include unreacted butenes, such as cis-2-butene, trans-2-butene, 1-butene, or combinations of two or more of these butenes. The metathesis catalyst 126 may also perform self-metathesis of 2-butene to 1-butene, and vice versa, in the metathesis reaction zone 120. Self-metathesis of butene with the metathesis catalyst 126 in the metathesis reaction zone 120 may be optional since the isomerization catalyst 124 may already perform the isomerization of 2-butene to 1-butene in the isomerization reaction zone 118. In one or more embodiments, the metathesis catalyst 126 may include a mesoporous silica catalyst support impregnated with a metal oxide.

The cracking reaction zone 122 of the multiple-stage catalyst system 110 may include a cracking catalyst 128 that may convert a portion of the unreacted 2-butene and the produced $C_5+$ olefins in the metathesis reaction product stream, which is produced in the metathesis reaction zone, to lighter olefins, such as ethylene and propene. Thus, the cracking reaction zone 122 may produce a cracking product stream (passed out of the cracking reaction zone 122 in the outlet stream 116) that may include propene, ethylene, or both. Other $C_4+$ hydrocarbons, such as butane or pentane that may be present in the metathesis reaction product stream, may also be converted to lighter alkanes and alkenes by the cracking catalyst 128 in the cracking reaction zone 122. In one or more embodiments, the cracking catalyst 128 may be a zeolite, such as a mordenite framework inverted (MFI) structured silica-containing catalyst.

In one or more embodiments, the multiple-stage catalyst system for producing propene from a stream containing butene may comprise an isomerization reaction zone having an isomerization catalyst that is MgO, a metathesis reaction zone downstream of the isomerization reaction zone and having a metathesis catalyst that is a mesoporous silica catalyst support impregnated with metal oxide, and a cracking reaction zone downstream of the metathesis reaction zone and having a cracking catalyst that is a MFI structured silica-containing catalyst.

Alternatively, in some embodiments, two or more of the isomerization catalyst 124, metathesis catalyst 126, or the cracking catalyst 128 may be admixed together in one or more mixed reaction zones. For example, referring to FIG. 6, in one or more embodiments, the multiple-stage catalyst system 110 may include a mixed isomerization and metathesis reaction zone 620 and a cracking reaction zone 622, which may be disposed downstream of the mixed isomerization and metathesis reaction zone 620. The mixed isomerization and metathesis reaction zone 620 may comprise an admixture of the isomerization catalyst 124, such as the MgO, and the metathesis catalyst 126, such as the mesoporous silica catalyst support impregnated with metal oxide. The cracking reaction zone 622 may comprise the cracking catalyst 128. The inlet stream 114 containing butene may enter the multiple-stage catalyst system 110 and be introduced to the mixed isomerization and metathesis reaction zone 620. The butene in the inlet stream 114 may be at least partially isomerized by the isomerization catalyst 124 and at least partially metathesized by the metathesis catalyst 126 in the mixed isomerization and metathesis reaction zone 620 to form the metathesis reaction product. The metathesis reaction product may then be passed to the cracking reaction zone 622, in which the metathesis reaction product may be at least partially cracked by the cracking catalyst 128 in the cracking reaction zone 622 to form a cracking reaction product. In some of these embodiments, the cracking reaction zone 622 may be a mixed metathesis and cracking reaction zone comprising an admixture of the metathesis catalyst 126 and the cracking catalyst 128.

Figure 7:
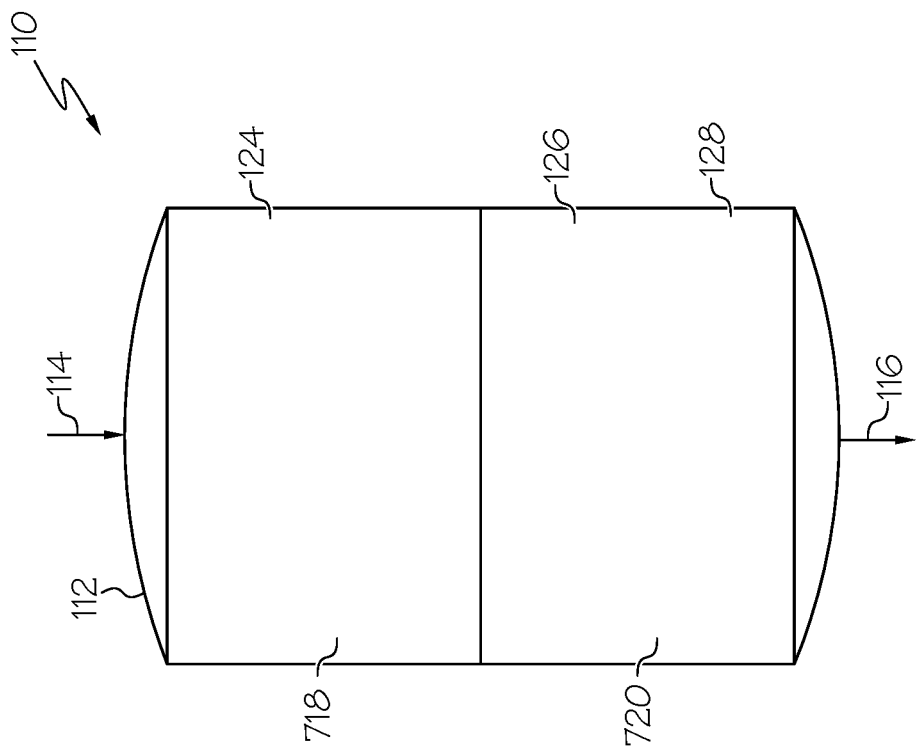
FIG. 7 schematically depicts another fixed bed continuous flow reactor including an isomerization catalyst, a metathesis catalyst, and a cracking catalyst, according to one or more embodiments of the present disclosure.

Referring to FIG. 7, in other embodiments, the multiple-stage catalyst system 110 may include an isomerization reaction zone 718 and a mixed metathesis and cracking reaction zone 720, which may be disposed downstream of the isomerization reaction zone 718. The isomerization reaction zone 718 may comprise the isomerization catalyst 124, which may be MgO. The mixed metathesis and cracking reaction zone 720 may comprise an admixture of the metathesis catalyst 126, such as the mesoporous silica catalyst support impregnated with metal oxide, and the cracking catalyst 128. The inlet stream 114 containing butene may enter the multiple-stage catalyst system 110 and be introduced to the isomerization reaction zone 718. The butene in the inlet stream 114 may be at least partially isomerized by the isomerization catalyst 124 in the isomerization reaction zone 718 to form an isomerization reaction product. The isomerization reaction product may then be passed to the mixed metathesis and cracking reaction zone 720. The isomerization reaction product may be at least partially metathesized by the metathesis catalyst 126 and at least partially cracked by the cracking catalyst 128 in the mixed metathesis and cracking reaction zone 720 to form the outlet stream 116, which may comprise a metathesis reaction product and a cracking reaction product. In some of these embodiments, the isomerization reaction zone 718 may be a mixed isomerization and metathesis reaction zone comprising an admixture of the the metathesis catalyst 126 and the isomerization catalyst 124.

Referring to FIG. 8, in one or more embodiments, the multiple-stage catalyst system 110 may comprise a single mixed reaction zone 734 comprising an admixture of the isomerization catalyst 124 (such as the MgO), the metathesis catalyst 126 (such as the mesoporous silica catalyst support impregnated by metal oxide), and the cracking catalyst 128. The inlet stream 114 containing butene may be introduced to the mixed reaction zone 734. The butene from the inlet stream 114 may be at least partially isomerized by the isomerization catalyst 124, at least partially metathesized by the metathesis catalyst 126, and at least partially cracked by the cracking catalyst 128 in the mixed reaction zone 734 to form an outlet stream 116 comprising propene.

Figure 6:
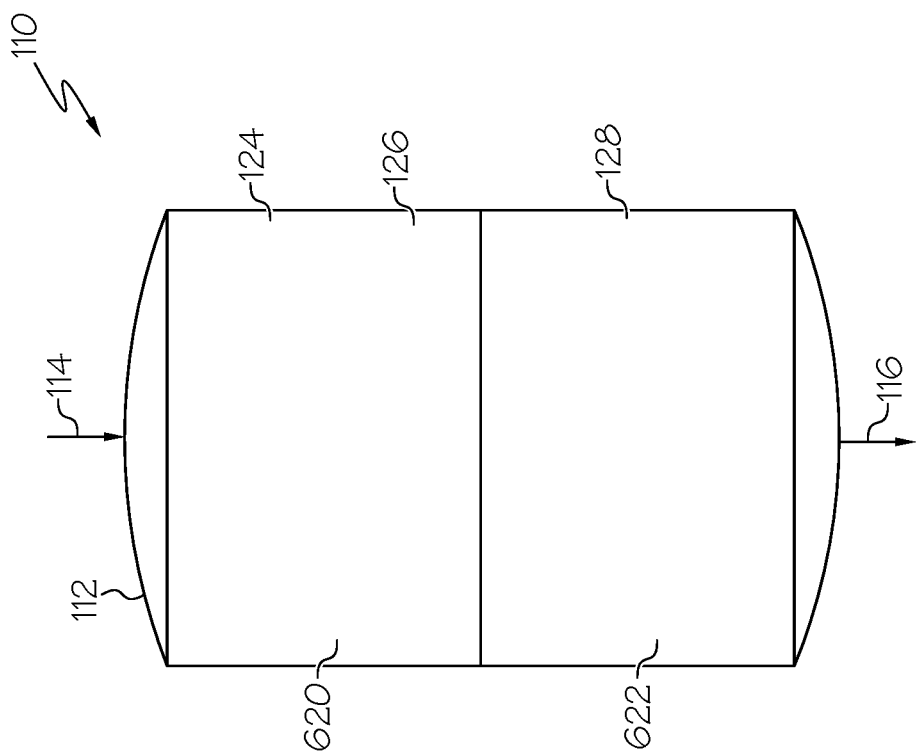
FIG. 6 schematically depicts another fixed bed continuous flow reactor including an isomerization catalyst, a metathesis catalyst, and a cracking catalyst, according to one or more embodiments of the present disclosure.
Figure 9:
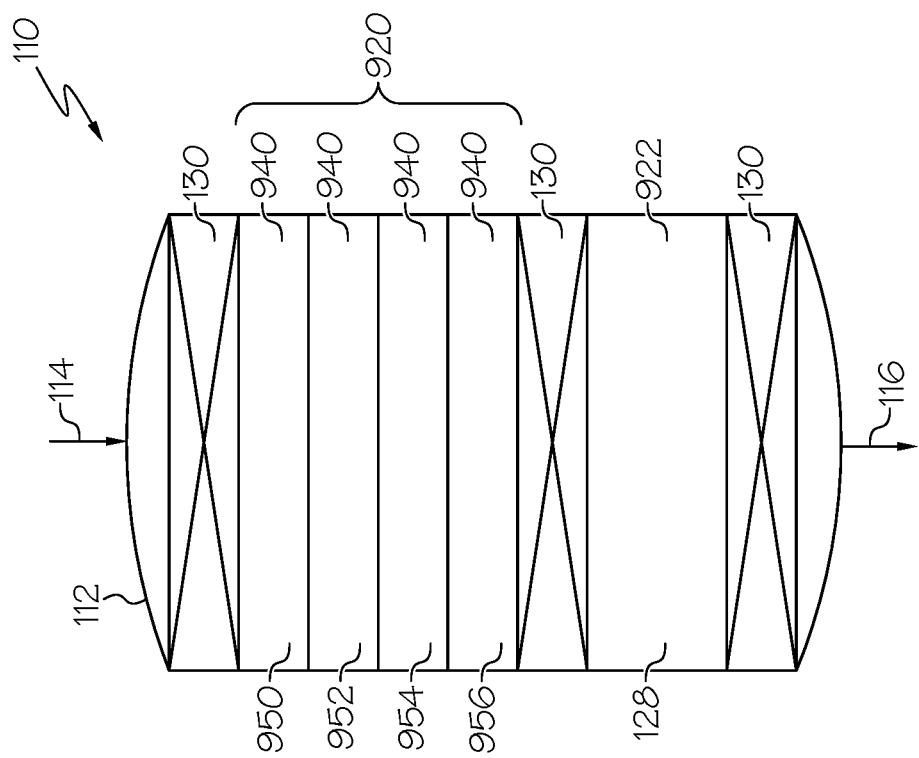
FIG. 9 schematically depicts another fixed bed continuous flow reactor including an isomerization catalyst, a metathesis catalyst, and a cracking catalyst, according to one or more embodiments of the present disclosure.

In one or more embodiments, the catalysts within a mixed reaction zone may be layered to create a catalyst gradient through the mixed reaction zone. For example, referring to FIG. 9, in one or more embodiments, the multiple-stage catalyst system 110 may include a mixed isomerization and metathesis reaction zone 920 and a cracking reaction zone 922. The mixed isomerization and metathesis reaction zone 920 may include a plurality of catalyst layers 940 that comprise an admixture of the isomerization catalyst 124 (FIG. 6) and the metathesis catalyst 126 (FIG. 6). Each of the catalyst layers 940 may have a different catalyst admixture comprising different ratios of the isomerization catalyst 124 and metathesis catalyst 126. For example, as shown in FIG. 9, the catalyst layer 940 proximal to the inlet stream 114 may comprise a first catalyst mixture 950 that is primarily the isomerization catalyst. Successive catalyst layers 940 may comprise a second catalyst mixture 952 and a third catalyst mixture 954 having progressively increasing ratios of metathesis catalyst. A fourth catalyst mixture 956 at the downstream end of the mixed isomerization and metathesis reaction zone 920 may have a greater amount of metathesis catalyst than isomerization catalyst. In one or more embodiments, the fourth catalyst mixture 956 at the downstream end of the mixed isomerization and metathesis reaction zone 920 may have a weight ratio of metathesis catalyst to isomerization catalyst of from 8:2 to 2:8, or from 6:4 to 4:6. Although the mixed isomerization and metathesis reaction zone 920 of FIG. 9 is illustrated and described as having four catalyst layers 940, it is understood that more than four catalyst layers 940 or less than four catalyst layers 940 may be utilized to create a gradient in catalyst concentration across the mixed isomerization and metathesis reaction zone 920 in the flow direction. In some embodiments, the multiple-stage catalyst system 110 may comprise a single mixed reaction zone having multiple catalyst layers with each of the catalyst layers comprising an admixture of the isomerization catalyst 124, metathesis catalyst 126, and cracking catalyst 128 having different ratios of the catalysts. As previously stated in this disclosure, it is understood that multiple methods for layering catalysts may be employed in the multiple-stage catalyst systems 110 described in this disclosure.

Referring back to FIG. 1, in one or more embodiments, the isomerization reaction zone 118, the metathesis reaction zone 120, and the cracking reaction zone 122 may be disposed in the reactor 112 with the isomerization reaction zone 118 positioned adjacent to the inlet stream 114 of the reactor 112, the metathesis reaction zone 120 positioned downstream of the isomerization reaction zone 118, and the cracking reaction zone 122 position downstream of the metathesis reaction zone 120. One or more additional reaction zones (not shown) may be disposed within the reactor 112 upstream or downstream of one or more of the isomerization reaction zone 118, metathesis reaction zone 120, and cracking reaction zone 122. As indicated previously in this disclosure, the discussion of a multiple-stage catalyst system having three reaction zones is merely for simplicity and a multiple-stage catalyst system with four or more reaction zones and four or more catalysts is also envisioned.

In some embodiments, each reaction zone 118, 120, 122 may be separated from each adjacent reaction zone by a separator 130, such as a layer of quartz wool. As used in this disclosure, the term "separator" may refer to a fluid permeable barrier between catalyst beds that substantially prevents solid catalyst particles in one catalyst bed from migrating to an adjacent catalyst bed, while allowing for reactants and products to move through the separator. The separator 130 may be chemically inert and generally makes no contribution to the reaction chemistry. Inserting the separator 130 between reaction zones 118, 120, 122 may maintain each catalyst 124, 126, 128 in its respective reaction zone 118, 120, 122 and prevent migration of different catalysts between reaction zones, which may lead to increased production of undesired by-products and decreased yield. In one or more embodiments, each reaction zone 118, 120, 122 may have a relatively small amount of the different types of catalysts from the other reaction zones, or may be completely free of catalysts from other reaction zones 118, 120, 122. For example, the isomerization reaction zone may comprise less than 10 wt. % of the metathesis or cracking catalyst from the other reaction zones, or even less than 5 wt. % of the metathesis or cracking catalysts from the other reaction zones. Additionally, the metathesis reaction zone may comprise less than 10 wt. % of the isomerization or cracking catalysts from the other reaction zones, or even less than 5 wt. % of the isomerization or cracking catalysts. Likewise, the cracking catalyst zone may comprise less than 10 wt. % of the isomerization or metathesis catalysts from the other reaction zones, or even less than 5 wt. % of the isomerization or metathesis catalysts. In some embodiments, each reaction zone 118, 120, 122 may be substantially free of different types of catalysts from other reaction zones so that each reaction zone 118, 120, 122 may contain less than 1 wt. % of different types of catalysts from other reaction zones. In other embodiments, each reaction zone 118, 120, 122 may also be positioned directly against each adjacent reaction zone without an intervening separator. In some embodiments, a layer of silicon carbide 132 may be positioned downstream of the cracking reaction zone 122, between a last reaction zone and the outlet stream 116 of the reactor 112. The silicon carbide 132 is chemically inert and makes no contribution to the reaction chemistry.

The isomerization catalyst in the isomerization reaction zone 118 of the multiple-stage catalyst system may isomerize 2-butene (which may be present in the inlet stream 114) to 1-butene, which may improve the overall yield of propene by the multiple-stage catalyst system 110. The isomerization catalyst may be a metal oxide, such as MgO, CaO, other metal oxide or combinations of these. In one or more embodiments, the isomerization catalyst may be MgO. MgO is generally compatible with the mesoporous silica catalyst support impregnated with tungsten oxide, which is a metathesis catalyst that may be used in the metathesis reaction zone in embodiments. An increased isomerization of 2-butene to 1-butene by the MgO ensures sufficient availability of both 2-butene and 1-butene for the cross-metathesis reaction that takes place in the metathesis reaction zone, which may result in an ultimate increase in concentrations of propene and $C_5+$ olefins in the metathesis product stream. The $C_5+$ olefins, such as propene, are further catalytically cracked by the cracking catalyst in the cracking reaction zone to further increase the yield of propene from the multiple-stage catalyst system 110. In one or more embodiments, CaO may be added as a co-catalyst to the MgO isomerization catalyst.

Use of MgO as the isomerization catalyst may also reduce the production of isobutene and other undesirable side-products in the metathesis reaction zone 120. The majority of the isobutene is produced in the cracking reaction zone 122, however small amounts of isobutene may be produced in the metathesis reaction zone 120 through one or more side reactions. The increased isomerization of the 2-butenes to 1-butene, and vice versa, with the MgO isomerization catalyst helps to maintain optimal proportions of 1-butene and 2-butenes in the metathesis reaction zone 120. By having the right amount of 1-butene and 2-butenes in the metathesis reaction zone 120, the cross-metathesis reaction is promoted, and the butenes are consumed in the cross-metathesis reaction rather than undergoing side reactions which produce the isobutene. By reducing the amounts of unreacted 1- and 2-butene, the amounts of isobutene are also reduced.

The isomerization of 2-butene to 1-butene by MgO may be completed at reaction temperatures of from 150 degrees Celsius (° C.) to 800° C., from 150° C. to 700° C., from 150° C. to 600° C., from 300° C. to 800° C., from 300° C. to 700° C., from 300° C. to 600° C., or from 300° C. to 550° C. These broad temperature ranges suitable for use with an MgO catalyst may allow the operating temperature of the entire multiple-stage catalyst system to be decreased in comparison to some dual stage catalyst systems without an MgO isomerization catalyst. In one or more embodiments, the reaction temperature of the isomerization of 2-butenes to 1-butene is from 300° C. to 550° C. A dual-stage catalyst system without the MgO relies upon the metathesis catalyst to self-metathesize the 2-butene to 1-butene. Without being bound by theory, it is believed that the MgO is capable of isomerizing 2-butene to 1-butene at a lower temperature than a temperature required to isomerize 2-butene to 1-butene through self-metathesis by the metathesis catalyst. The lower reactor operating temperatures that are capable using an MgO isomerization catalyst may lead to an increase in propene yield from the multiple-stage catalyst system. The lower operating temperature also provides the immediate benefit of lower operating costs from less required heating.

In one or more embodiments, the MgO may be used to remove contaminants from the stream containing butene or other feed stream. Metathesis catalysts may be sensitive to poisons, such as peroxides, water, carbon dioxide, oxygenates, heavy metals, nitrogen compounds, and sulfur compounds, which may have a deleterious effect on the performance of the metathesis catalyst. MgO is capable of removing some poisons, such as peroxides, for example, that may be present in the stream containing butene or other feed streams in low concentrations. In some embodiments, the MgO catalyst may be used as a guard-bed for the metathesis catalyst by removing or destroying traces of contaminants or poisons which may be present in the stream containing butene. By serving as a guard bed, the MgO may reduce fouling of the metathesis catalyst activity, which may result in improved yield of propene and longer service life of the metathesis catalyst in the metathesis reaction zone. MgO may further enhance conversion of butene to propene through generation of gas-phase "excited species," such as allyl or allyl-oxo radicals, for example, which may be initiators or precursors of metathesis sites. By generating initiators or precursors of metathesis sites, the MgO may further enhance the metathesis activities of the multi-stage catalyst system.

The MgO may have a mean average particle size of from 100 nanometers (nm) to 500 nm, from 100 nm to 400 nm, from 100 nm to 375 nm, from 200 nm to 500 nm, from 200 nm to 400 nm, or from 200 nm to 375 nm. In one or more embodiments, the MgO may have a mean average particle size from 100 nm to 400 nm. In one or more embodiments, the MgO may have a mean average particle size from 200 nm to 400 nm. Physical properties of the MgO catalyst can be determined using a nano particle size analyzer, such as those available from Horiba Scientific.

In embodiments, the MgO may have a total pore volume of from 0.05 cubic centimeters per gram ($cm^3/g$) to 0.5 $cm^3/g$, from 0.05 $cm^3/g$ to 0.4 $cm^3/g$, from 0.1 $cm^3/g$ to 0.5 $cm^3/g$, or from 0.1 $cm^3/g$ to 0.4 $cm^3/g$. The MgO catalyst may have an average pore size of from 5 nm to 50 nm, from 5 nm to 40 nm, from 5 nm to 30 nm, from 10 nm to 50 nm, from 10 nm to 40 nm, from 10 nm to 30 nm, from 20 nm to 50 nm, from 20 nm to 40 nm, or from 20 nm to 30 nm. The MgO may have a surface area of 50 square meters per gram ($m^2/g$) to 250 $m^2/g$, from 50 $m^2/g$ to 225 $m^2/g$, from 50 $m^2/g$ to 200 $m^2/g$, from 50 $m^2/g$ to 175 $m^2/g$, from 75 $m^2/g$ to 250 $m^2/g$, from 75 $m^2/g$ to 200 $m^2/g$, from 75 $m^2/g$ to 175 $m^2/g$, from 100 $m^2/g$ to 250 $m^2/g$, from 100 $m^2/g$ to 225 $m^2/g$, from 100 $m^2/g$ to 200 $m^2/g$, or from 100 $m^2/g$ to 175 $m^2/g$.

Commercially available MgO, such as Sigma Aldrich Product Number 342793 (>99% trace metals basis), for example, may be used as a starting material in preparing the MgO isomerization catalyst. Additionally, MgO may be prepared using a co-precipitation method, in which the MgO synthesized from the reaction of a magnesium nitrate compound, such as magnesium nitrate hexahydrate, and ammonium hydroxide. The MgO resulting from this reaction precipitates out of the reaction solution as a white solid, which may then be separated, washed, and dried. Preparation of MgO by co-precipitation is described subsequently in this disclosure in Example 2. Other methods of synthesizing MgO using other precursors are also contemplated by this disclosure, such as synthesizing magnesium carbonate and calcining the magnesium carbonate to MgO. The basicity, pore volume, and surface area of the MgO may vary with the synthesis method utilized to make the MgO.

Prior to use of the MgO as the isomerization catalyst in the multiple-stage catalyst system, the MgO may be pretreated to activate the sites responsible for butene isomerization. The MgO may be pretreated by calcination in a calcination oven. MgO is generally basic in nature and the basicity of the MgO may be influenced by the calcination temperature and process, in particular, calcination conditions may influence the strength and quantity of basic reaction sites in the MgO catalyst. Selection of the appropriate calcination temperature may enhance the number and strength of the basic sites in the MgO, thus, enhancing the isomerization performance of the MgO catalyst. The calcination temperature and ramping rate of the calcining process may influence the performance of the MgO catalyst, which may influence the selectivity of the multiple-stage catalyst system. The "calcination temperature" is a target average temperature to which the MgO is heated and at which the MgO is calcined over a period of time during the calcination process. The "ramping rate," as used in this disclosure, is a rate at which the temperature of the MgO is increased from a starting temperature to the calcination temperature. The MgO may be placed in the calcination oven and the temperature of the calcination oven may be increased at the ramping rate to the calcination temperature. Then, the MgO may be maintained at the calcination temperature for a predetermined period of time. At the end of the predetermined period of time, the calcined MgO may be allowed to slowly cool down to ambient temperature. Calcination of MgO is described subsequently in the present disclosure in Example 1.

The MgO may be calcined at a calcination temperature of from 300° C. to 800° C., from 300° C. to 700° C., from 300° C. to 650° C., from 300° C. to 600° C., from 400° C. to 800° C., from 400° C. to 700° C., from 400° C. to 650° C., from 400° C. to 600° C., from 500° C. to 800° C., from 500° C. to 700° C., from 500° C. to 650° C., or from 500° C. to 600° C. In one or more embodiments, the MgO is calcined at a calcination temperature of at least 500° C. In one or more embodiments, the MgO is calcined at a calcination temperature of from 300° C. to 800° C. In one or more embodiments, the MgO is calcined at a calcination temperature of from 400° C. to 700° C. The ramping rate of the calcination process may be 1 degree Celsius per minute (° C./min) to 4° C./min, from 1° C./min to 3° C./min, from 1° C./min to 2.5° C./min, from 1° C./min to 2° C./min, from 1.5° C./min to 4° C./min, from 1.5° C./min to 3° C./min, from 1.5° C./min to 2.5° C./min, from 1.75° C./min to 4° C./min, from 1.75° C./min to 3° C./min, from 1.75° C./min to 2.5° C./min, or from 1.75° C./min to 2.25° C./min. The MgO may be calcined in the calcination oven for a predetermined period of time from 1.5 hours (hr.) to 5 hr., from 1.5 hr. to 4 hr., from 1.5 hr. to 3.5 hr., from 1.5 hr. to 3 hr., from 1.5 hr. to 2 hr., from 2 hr. to 5 hr., from 2 hr. to 4.5 hr., from 2 hr. to 4 hr., from 2 hr. to 3.5 hr., from 2.5 hr. to 5 hr., from 2.5 hr. to 4 hr., from 2.5 hr. to 3.5 hr., from 2.5 hr. to 3 hr., from 2.25 hr. to 2.75 hr., or from 2.25 hr. to 3 hr. The MgO isomerization catalyst may also be subjected to one or more additional pre-treatment processes to enhance activity of the catalyst.

For example, following calcination, the MgO may be subjected to carbon dioxide (CO) gas, hydrogen ($H_2$) gas, or both CO and $H_2$ for a period of from 10 minutes to 20 minutes, or about 15 minutes prior to commencing flow of reactants to the MgO.

As described previously in this disclosure, the metathesis catalyst may be a mesoporous silica catalyst support impregnated with a metal oxide. Various materials are contemplated for the mesoporous silica catalyst support, for example, one or more molecular sieves or zeolites. As used in the present disclosure, "mesoporous" refers to a material having an average pore size of greater than 2 nanometers and less than 50 nanometers. The average pore size may be obtained from the average surface area and pore size distribution, which are determined using the BET method subsequently described in this disclosure. Average pore size is generally determined as a pore diameter or pore radius based on the assumption of cylindrical shaped pores. However, it is understood that catalysts described in this disclosure may have actual shapes that are cylindrical or other shapes, such as, but not limited to, conical, square, slit-shaped, or other irregular shaped pores or combinations of these. In this disclosure, the average pore size is reported as an average pore diameter. The mesoporous silica catalyst support impregnated with metal oxide may have a relative pore volume per weight of material of at least 0.6 cubic centimeters per gram ($cm^3/g$). Without being bound by theory, the present pore size distribution and pore volume of the mesoporous silica-alumina catalyst support impregnated with metal oxide may be sized to achieve better catalytic activity and reduced blocking of pores by metal oxides, whereas smaller pore volume and pore size catalyst systems may be susceptible to pore blocking and thereby reduced catalytic activity.

In one or more embodiments, the average pore size of the mesoporous silica-alumina catalyst support impregnated with metal oxide may be from 2 nanometers (nm) to 50 nm, from 2.5 nm to 40 nm, from 2.5 nm to 30 nm, from 2.5 nm to 20 nm, from 2.5 nm to 18 nm, from 2.5 nm to 12 nm, from 2.5 nm to 4.5 nm, from 2.5 nm to 3.5 nm, from 8 nm to 12 nm, from 8 nm to 18 nm, from 8 nm to 20 nm, from 8 nm to 40 nm, from 12 nm to 18 nm, or from 12 nm to 40 nm.

In one or more embodiments, the relative pore volume per weight of the mesoporous silica-alumina catalyst support impregnated with metal oxide may be from 0.6 centimeters cubed per gram ($cm^3/g$) to 2.5 $cm^3/g$, from 0.6 $cm^3/g$ to 1.5 $cm^3/g$, from 0.6 $cm^3/g$ to 1.3 $cm^3/g$, from 0.6 $cm^3/g$ to 1.1 $cm^3/g$, from 0.6 $cm^3/g$ to 0.9 $cm^3/g$, from 0.7 $cm^3/g$ to 0.9 $cm^3/g$, from 0.7 $cm^3/g$ to 1.1 $cm^3/g$, from 0.7 $cm^3/g$ to 1.3 $cm^3/g$, from 0.7 $cm^3/g$ to 1.5 $cm^3/g$, from 0.7 $cm^3/g$ to 2.5 $cm^3/g$, from 0.8 $cm^3/g$ to 1.3 $cm^3/g$, from 0.8 $cm^3/g$ to 1.5 $cm^3/g$, or from 0.8 $cm^3/g$ to 2.5 $cm^3/g$. In some embodiments, the mesoporous silica-alumina catalyst support impregnated with metal oxide may have a relative pore volume per weight of the mesoporous silica-alumina catalyst support impregnated with metal oxide of at least 0.6 $cm^3/g$.

Moreover, while broader ranges are contemplated, the mesoporous silica-alumina catalyst support impregnated with metal oxide, in one or more embodiments, may include a surface area per weight of the mesoporous silica-alumina catalyst support impregnated with metal oxide of from 200 meters squared per gram ($m^2/g$) to 600 $m^2/g$. In other embodiments, the mesoporous silica-alumina catalyst support impregnated with metal oxide may have a surface area from 200 $m^2/g$ to 350 $m^2/g$, from 200 $m^2/g$ to 325 $m^2/g$, from 200 $m^2/g$ to 300 $m^2/g$, from 225 $m^2/g$ to 600 $m^2/g$, from 225 $m^2/g$ to 350 $m^2/g$, from 225 $m^2/g$ to 325 $m^2/g$, from 225 $m^2/g$ to 300 $m^2/g$, from 250 $m^2/g$ to 600 $m^2/g$, from 250 $m^2/g$ to 350 $m^2/g$, from 250 $m^2/g$ to 325 $m^2/g$, from 250 $m^2/g$ to 300 $m^2/g$, from 300 $m^2/g$ to 325 $m^2/g$, or from 300 $m^2/g$ to 350 $m^2/g$.

The mesoporous silica-alumina catalyst support impregnated with metal oxide may have an mean particle size of from 20 nm to 200 nm, from 20 nm to 150 nm, from 20 nm to 100 nm, from 20 nm to 75 nm, from 50 nm to 200 nm, from 50 nm to 150 nm, from 50 nm to 125 nm, from 50 nm to 75 nm, from 75 nm to 200 nm, from 75 nm to 150 nm, or from 75 nm to 125 nm. The mesoporous silica-alumina catalyst support impregnated with metal oxide may have a mean particle size distribution of from 100 angstroms (Å) to 300 Å, from 100 Å to 250 Å, from 100 Å to 200 Å, from 120 Å to 300 Å, from 120 Å to 250 Å, and from 120 Å to 200 Å. The mean particle size and mean particle size distribution can be measured using a particle size analyzer, such as a Nanopartica™ series particle size analyzer from Horiba Scientific Company, which measures the size of single particles dispersed in water using ultraviolet (UV) light.

Further, the mesoporous silica catalyst may have a total acidity from 0.001 millimole/gram (mmol/g) to 0.5 mmol/g, from 0.01 mmol/g to 0.5 mmol/g, from 0.1 mmol/g to 0.5 mmol/g, from 0.3 mmol/g to 0.5 mmol/g, from 0.4 mmol/g to 0.5 mmol/g, from 0.001 mmol/g to 4 mmol/g, or from 0.001 mmol/g to 0.3 mmol/g. The acidity may be generally maintained at or less than 0.5 mmol/g to yield the desired propene selectivity of the multiple-stage catalyst system and to reduce production of undesirable byproducts, such as aromatics. Increasing acidity may increase the overall butene conversion; however, this increased conversion may lead to decreased propene selectivity and increased production of aromatic byproducts, which may lead to catalyst coking and deactivation.

For the mesoporous silica catalyst impregnated with metal oxide, the metal oxide may include one or more oxides of a metal from Groups 6-10 of the IUPAC Periodic Table. In some embodiments, the metal oxide may include one or more oxides of molybdenum, rhenium, tungsten, or any combination of these. In one or more embodiments, the metal oxide of the mesoporous silica catalyst support impregnated with metal oxide is tungsten oxide ($WO_3$). It is contemplated that various amounts of metal oxide may be impregnated into the mesoporous silica catalyst support. For example and not by way of limitation, the weight percentage (wt. %) of metal oxide, for example, $WO_3$, in the mesoporous silica catalyst is from 1 wt. % to 30 wt. %, from 1 wt. % to 25 wt. %, from 1 wt. % to 20 wt. %, from 1 wt. % to 15 wt. %, from 5 wt. % to 30 wt. %, from 5 wt. % to 25 wt. %, from 5 wt. % to 20 wt. %, from 5 wt. % to 15 wt. %, from 8 wt. % to 30 wt. %, from 8 wt. % to 25 wt. %, from 8 wt. % to 20 wt. %, from 8 wt. % to 15 wt. %, from 8 wt. % to 12 wt. %, from 10 wt. % to 30 wt. %, or from 10 wt. % to 20 wt. %. In one or more embodiments, the mesoporous silica catalyst support impregnated with metal oxide includes from 1 wt. % to 30 wt. % tungsten oxide. In one or more embodiments, the mesoporous silica catalyst support impregnated with metal oxide includes from 8 wt. % to 12 wt. % tungsten oxide. The amount of tungsten oxide impregnated onto the mesoporous silica catalyst support may be verified using inductively coupled plasma (ICP) mass spectrometer or an x-ray fluorescence (XRF) spectrometer to determine the amount of tungsten in a sample of the mesoporous silica catalyst support impregnated with tungsten oxide Various silica structures are contemplated for the cracking catalyst. The cracking catalyst may be a zeolite. In some embodiments, the cracking catalyst may be a structured zeolite, such as MFI or BEA structured zeolite, for example. In one or more embodiments, the cracking catalyst may be a MCM-41 catalyst or a SBA-15 catalyst. In one or more embodiments, the cracking catalyst may be an MFI structured silica catalyst. For example, the MFI structured silica-containing catalyst may include MFI structured aluminosilicate zeolite catalysts or MFI structured silica catalysts that do not contain alumina or are substantially free of alumina. In one or more embodiments, the MFI structured silica-containing catalyst includes alumina. In other embodiments, the MFI structured silica-containing catalyst is substantially free of alumina, having less than 1 wt. % alumina. In one or more embodiments, the MFI structured silica-containing catalysts may have less than 0.01 wt. % of alumina.

Moreover, it is contemplated that the MFI structured silica-containing catalyst may include other impregnated metal oxides in addition to or as an alternative to alumina Like the mesoporous silica catalyst, the MFI structured silica-containing catalysts may have alumina, metal oxides, or both impregnated in the silica support. In addition to or as a substitute for alumina, it is contemplated that the MFI structured silica-containing catalyst includes one or more of the metal oxides previously listed in this disclosure, specifically, one or more oxides of a metal from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites.

For the MFI structured aluminosilicate zeolite catalysts, various amounts of alumina are contemplated. In one or more embodiments, the MFI structured aluminosilicate zeolite catalysts may have a molar ratio of silica to alumina of from 5 to 5000, from 5 to 4000, from 5 to 3000, from 5 to 2500, from 100 to 5000, from 100 to 4000, from 100 to 3000, from 100 to 2500, from 200 to 5000, from 200 to 4000, from 200 to 3000, from 200 to 2500, from 1000 to 5000, from 1000 to 4000, from 1000 to 3000, from 1000 to 2500, from 1500 to 5000, from 1500 to 4000, from 1500 to 3000, or from 1500 to 2500. Various suitable commercial embodiments of the MFI structured aluminosilicate zeolite catalysts are contemplated, for example, ZSM-5 zeolites such as MFI-280 produced by Zeolyst International or MFI-2000 produced by Saudi Aramco. Preparation of the MFI-2000 cracking catalyst is described subsequently in this disclosure in Example 5.

Various suitable commercial embodiments are also contemplated for the alumina free MFI structured silica-containing catalysts. One such example is Silicalite-1 produced by Saudi Aramco. Preparation of Silicalite-1 is subsequently described in this disclosure in Example 4.

The MFI structured silica-containing catalyst may include an average pore size of from 1.5 nm to 3 nm, or from 1.5 nm to 2.5 nm. Further, the MFI structured silica-containing catalyst may have an average relative pore volume per weight of material of from 0.1 cm$^3$/g to 0.3 cm$^3$/g, or from 0.15 cm$^3$/g to 0.25 cm$^3$/g. The MFI structured silica-containing catalyst may have an average surface area of from 300 m$^2$/g to 425 m$^2$/g, or from 340 m$^2$/g to 410 m$^2$/g. Additionally, the MFI structured silica-containing catalyst may have a total acidity of from 0.001 mmol/g to 0.1 mmol/g, or from 0.01 mmol/g to 0.08 mmol/g. The acidity may be maintained at or less than 0.1 mmol/g to reduce production of undesirable byproducts, such as aromatics. Increasing acidity may increase the amount of cracking; however, this increased cracking may also lead to less selectivity and increased production of aromatic byproducts, which may lead to catalyst coking and deactivation.

In some cases, MFI structured silica-containing catalyst may be modified with an acidity modifier to adjust the level of acidity in the MFI structured silica-containing catalyst. For example, these acidity modifiers may include rare earth modifiers, phosphorus modifiers, potassium modifiers, or combinations of each. However, as the present embodiments are focused on reducing the acidity to a level at or less than 0.1 mmol/g, the present structured silica catalysts may be free of acidity modifiers, such as those selected from rare earth modifiers, phosphorus modifiers, potassium modifiers, or combinations of each. As used in the present disclosure, "free of acidity modifiers" means less than 0.01% by weight of acidity modifier in the MFI structured silica-containing catalyst.

Additionally, in some embodiments, the MFI structured silica-containing catalyst may have an individual crystal size of from 10 microns to 40 microns, from 15 microns to 40 microns, or from 20 microns to 30 microns. In other embodiment, the MFI structured silica-containing catalyst may have an individual crystal size of from 1 micron to 5 microns.

Moreover, various amounts of each catalyst are contemplated for the present multiple-stage catalyst system. For example, it is contemplated that the ratio by volume of the isomerization catalyst to the metathesis catalyst to the cracking catalyst may be from 5:1:1 to 1:5:1 to 1:1:5, from 2:1:1 to 1:2:1 to 1:1:2, or 1:1:1. The volumetric ratio of the MgO in the isomerization reaction zone to the mesoporous silica catalyst support impregnated with metal oxide in the metathesis reaction zone may be from 1:2 to 5:1, from 1:2 to 4:1, from 1:2 to 3:1, from 1:2 to 2:1, from 1:2 to 1:1, from 1:1 to 5:1, from 1:1 to 4:1, from 1:1 to 3:1, from 1:1 to 2:1, from 2:1 to 4:1, or from 2:1 to 3:1. In one or more embodiments, the volumetric ratio of the MgO in the isomerization reaction zone to the mesoporous silica catalyst support impregnated with metal oxide in the metathesis reaction zone may be at least 1:2. In other embodiments, the volumetric ratio of the MgO in the isomerization reaction zone to the mesoporous silica catalyst support impregnated with metal oxide in the metathesis reaction zone may be at least 1:1.

Various methods of making the metathesis and cracking catalysts used in the multiple-stage catalyst system are contemplated. Specifically, the processes of wet impregnation and hydrothermal synthesis may be utilized; however, other catalyst synthesis techniques are also contemplated.

It is contemplated that the isomerization catalyst, the metathesis catalyst, and the cracking catalyst may be disposed in one reactor or in multiple reactors. For example, it may be desirable to use separate reactors for one or more of the isomerization catalyst, metathesis catalyst, or cracking catalyst when they operate at different environmental conditions, including temperature and pressure. Regardless of whether one or multiple reactors contain the multiple catalysts, the multiple-stage catalyst system may have the isomerization catalyst zone, the metathesis catalyst zone downstream of the isomerization zone, and the cracking catalyst zone downstream of the metathesis zone.

Referring again to FIG. 1, in a non-limiting example of a down flow reactor 112 in which the inlet stream 114 containing butene enters from the top of the reactor 112, the isomerization catalyst 124 may be located adjacent to or in a top part of the reactor 112, the metathesis catalyst 126 may be located in a middle part of the reactor 112, and the cracking catalyst 128 may be disposed in a bottom part of the reactor 112. In another non-limiting example, each catalyst may be positioned as discrete catalyst beds within the reactor 112. Moreover, it is contemplated that the multiple catalysts of the multiple-stage catalyst system 110 may be in contact with one or more of the other catalysts or separated by a separator 130 as previously described in this disclosure. However, if the multiple catalysts are in contact, it is desirable that the isomerization catalyst 124 is still disposed upstream of the metathesis catalyst 126 and that the metathesis catalyst 126 is still disposed upstream of the cracking catalyst 128.

The catalysts may be used in the same reactor or with different reactors arranged in series. Alternatively, it is contemplated that the isomerization catalyst is disposed in a first reactor, the metathesis catalyst is disposed in a separate second reactor downstream of the first reactor, and the cracking catalyst is disposed in a separate third reactor downstream of the second reactor. Additionally, it is contemplated that the isomerization catalyst is disposed in a first reactor, the cracking catalyst is disposed in a separate second reactor downstream of the first reactor, and the metathesis catalyst is disposed in the first reactor downstream of the isomerization catalyst or in the second reactor upstream of the cracking catalyst. Further, it is contemplated that one or more reactors may comprise admixtures of two or more of the isomerization catalyst, the metathesis catalyst, or the cracking catalyst. In embodiments, direct conduits may extend between the first reactor and second reactor and between the second reactor and third reactor, so that the cracking catalyst may directly crack the product of the butene cross-metathesis reaction.

Referring again to FIG. 1, various operating conditions are contemplated for contacting the stream containing butene with the multiple-stage catalyst system 110. For example, the stream containing butene (for example, the inlet stream 114) may contact the multiple-stage catalyst system 110 at a space hour velocity of from 10 per hour ($h^{-1}$) to 10,000 $h^{-1}$, from 10 $h^{-1}$ to 5000 $h^{-1}$, from 10 $h^{-1}$ to 2500 $h^{-1}$, from 10 $h^{-1}$ to 1200 $h^{-1}$, from 100 $h^{-1}$ to 10,000 $h^{-1}$, from 100 $h^{-1}$ to 5000 $h^{-1}$, from 100 $h^{-1}$ to 2500 $h^{-1}$, from 100 $h^{-1}$ to 1200 $h^{-1}$, from 300 $h^{-1}$ to 10,000 $h^{-1}$, from 300 $h^{-1}$ to 5000 $h^{-1}$, from 300 $h^{-1}$ to 2500 $h^{-1}$, from 300 $h^{-1}$ to 1200 $h^{-1}$, from 500 $h^{-1}$ to 10,000 $h^{-1}$, from 500 $h^{-1}$ to 5000 $h^{-1}$, from 500 $h^{-1}$ to 2500 $h^{-1}$, or from 500 $h^{-1}$ to 1200 $h^{-1}$.

The stream containing butene (for example, the inlet stream 114) may contact the multiple-stage catalyst system 110 at a temperature of from 200° C. to 600° C., from 200° C. to 550° C., from 200° C. to 500° C., from 200° C. to 450° C., from 200° C. to 400° C., from 200° C. to 350° C., from 300° C. to 600° C., from 300° C. to 550° C., from 300° C. to 500° C., from 300° C. to 450° C., from 300° C. to 400° C., from 300° C. to 350° C., from 350° C. to 600° C., from 350° C. to 550° C., from 350° C. to 500° C., from 350° C. to 450° C., from 350° C. to 400° C., from 400° C. to 600° C., from 400° C. to 550° C., from 400° C. to 500° C., or from 400° C. to 450° C. In one or more embodiments, the isomerization, the metathesis, and the cracking reactions are performed at a temperature of from 400° C. to 600° C. Furthermore, the inlet stream 114 containing butene may contact the multiple-stage catalyst system 110 at a pressure of from 1 bar to 30 bars, from 1 bar to 20 bars, from 1 bar to 10 bars, from 2 bars to 30 bars, from 2 bars to 20 bars, or from 2 bars to 10 bars. In one or more embodiments, the inlet stream 114 containing butene may contact the multiple-stage catalyst system 110 at atmospheric pressure.

Optionally, the isomerization, the metathesis, and the cracking catalysts may be pretreated prior to the isomerization, metathesis, and cracking. For example, the catalysts in the multiple-stage catalyst system may be pretreated by passing a heated gas stream through the multiple-stage catalyst system a pretreatment period. The gas stream may include one or more of an oxygen-containing gas, nitrogen gas ($N_2$), carbon monoxide (CO), hydrogen gas ($H_2$), a hydrocarbon gas, air, other inert gas, or combinations of these gases. The temperature of the heated gas stream may be from 250° C. to 700° C., from 250° C. to 650° C., from 250° C. to 600° C., from 250° C. to 500° C., from 300° C. to 700° C., from 300° C. to 650° C., from 300° C. to 600° C., from 300° C. to 500° C., from 400° C. to 700° C., from 400° C. to 650° C., from 400° C. to 600° C., or from 400° C. to 500° C. The pretreatment period may be from 1 minute (min) to 30 hours (hr), from 1 min to 20 hr, from 1 min to 10 hr, from 1 min to 5 hr, from 0.5 hr to 30 hr, from 0.5 hr to 20 hr, from 0.5 hr to 10 hr, from 0.5 hr to 5 hr, from 1 hr to 30 hr, from 1 hr to 20 hr, from 1 hr to 10 hr, from 1 hr to 5 hr, from 5 hr to 30 hr, from 5 hr to 20 hr, or from 5 hr to 10 hr. In one or more embodiments, for example, the multiple-stage catalyst system may be pretreated with $N_2$ for a pretreatment period of from 1 hour to 5 hours before commencing isomerization, metathesis, and cracking and at a pretreating temperature of at least 400° C., or at least 500° C. In another embodiment, the multiple-stage catalyst system may be pretreated with air for a period of from 10 hr to 15 hr prior to commencing isomerization, metathesis, and cracking, the air being at a temperature of at least 400° C.

A process for producing propene includes at least partially isomerizing butene in the isomerization reaction zone that includes an isomerization catalyst to form an isomerization reaction product. As previously described in this disclosure, the isomerization catalyst may be MgO. The process also includes at least partially metathesizing the isomerization reaction product in the metathesis reaction zone that includes a metathesis catalyst to form a metathesis reaction product, since cross-metathesis occurs at a faster rate to produce propene. As previously described in this disclosure, the metathesis catalyst may be a mesoporous silica catalyst support impregnated with metal oxide. The process also includes partially cracking the metathesis reaction product in the cracking reaction zone that includes a cracking catalyst to form a cracking reaction product. The metathesis reaction zone may be downstream of the isomerization reaction zone, and the cracking reaction zone may be downstream of the metathesis reaction zone. In one or more embodiments of the process, the isomerization reaction zone, metathesis reaction zone, and the cracking reaction zone may be disposed within a reactor. In one or more embodiments, the isomerization reaction product may include 1-butene and 2-butene. In one or more embodiments, the metathesis reaction product may include propene and pentene. In one or more embodiments, the cracking reaction product may include propene.

The process for producing propene may include introducing a stream comprising butene to the isomerization reaction zone that includes the isomerization catalyst, at least partially isomerizing and activating the stream comprising butene in the isomerization reaction zone to form an isomerization reaction product stream, passing the isomerization reaction product stream to the metathesis reaction zone that includes the metathesis catalyst, at least partially metathesizing the isomerization reaction product stream with the metathesis catalyst to form a metathesis reaction product stream, passing the metathesis reaction product stream to a cracking reaction zone that includes a cracking catalyst, and at least partially cracking the metathesis reaction product stream with the cracking catalyst to form a cracking reaction product stream that includes propene. In one or more embodiments, the process for producing propene from a stream containing butene may include calcining the MgO isomerization catalyst.

In one or more embodiments, the isomerization reaction product stream may include 1-butene and 2-butene. In some embodiments, the 2-butene in the isomerization reaction product stream may include cis-2-butene, trans-2-butene, or both. In some embodiments, the metathesis reaction product stream may include propene and pentene. In some embodiments, the metathesis reaction product may further include one or more of unreacted 2-butene, unreacted 1-butene, and $C_6+$ olefins.

In one or more embodiments, the cracking reaction product stream produced by the multiple-stage catalyst system may have at least an 80 mol. % conversion of butene and a propene yield in mol. % of at least 30%. In some embodiments, the cracking reaction product stream may have at least an 85 mol. % conversion of butene and a propene yield in mol. % of at least 40%. In some embodiments, the product stream may have at least a 10 mol. % yield of ethylene, or at least a 15 mol. % yield of ethylene, or at least a 20 mol. % yield of ethylene. In other embodiments, the product stream may have at least 45 mol. % yield of propene, or at least a 50 mol. % yield of propene. In one or more embodiments, the multi-stage catalyst system and propene processes of the present disclosure may produce propene from butene without introducing externally added ethylene into the stream containing butene or into the reactor as a supplemental feed stream. In one or more embodiments, the multi-stage catalyst system and propene processes of the present disclosure may produce propene from a butene containing stream that has less than 5 wt. % ethylene, or less than 1 wt. % ethylene.

Moreover, the cracking reaction product stream may include less than 1 wt. % aromatics. The cracking reaction product stream may also have less than 5 wt. % of alkanes and aromatics. Without being bound by theory, in some embodiments it may be desirable that the aromatics and alkanes yield be low as it indicates coke formation, which may result in catalyst deactivation.

EXAMPLES

The following examples show the preparation of various catalysts which are used in combination as in the presently disclosed multiple-stage catalyst systems.

Example 1: Preparation of MgO Catalyst from Commercially Available MgO

To prudently prepare the MgO catalyst, commercially available MgO was obtained from Sigma Aldrich (Product No. 342793, >99% trace metals basis, Lot No. MKBQ2256V). 4 grams of the commercially available MgO was calcined in a calcination oven under air at a ramping rate of 2° C. per minute until the MgO attained a temperature of 550° C. The MgO was then maintained in the calcination oven at a temperature of 550° C. for 150 minutes. Following calcination, the MgO was maintained in the calcination oven and allowed to slowly cool down to room temperature. MgO catalyst prepared from commercially available MgO according to the above-described method is referred to subsequently as the catalyst of Example 1 or the MgO of Example 1.

Figure 2:
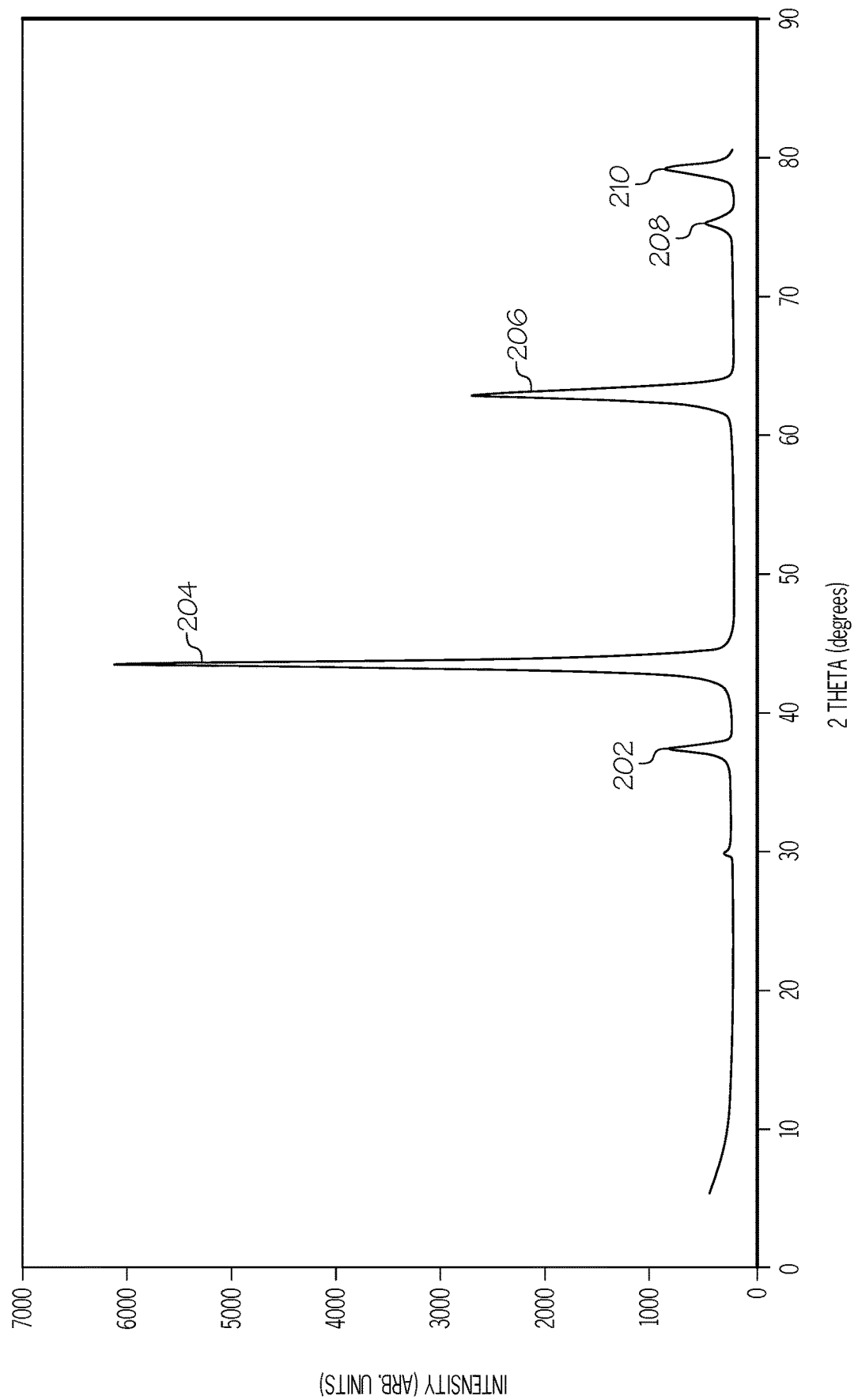
FIG. 2 is an X-ray diffraction (XRD) graph illustrating the XRD profile of a MgO catalyst prepared, in accordance with one or more embodiments of the present disclosure.

The XRD profile of the MgO catalyst of Example 1 is shown in FIG. 2. The diffraction peaks corresponding to the crystalline MgO of Example 1 may be observed in FIG. 2 at 2 theta (2θ)=37.0° (reference number 202), 43.0° (reference number 204), 62.4° (reference number 206), 74.8° (reference number 208), and 78.7° (reference number 210). See, J. Puriwat et al., Catalysis Communications, 12 (2010) 80-85.

Example 2: Preparation of MgO Catalyst Using the Co-Precipitation Method

The MgO catalyst was also prepared using a co-precipitation technique. 25.64 grams of magnesium nitrate hexahydrate $[Mg(NO_3)_2.6H_2O]$ was mixed with 100 milliliters (ml) of deionized water (DI water) in a first beaker to form a first $Mg(NO_3)_2$ solution. In a second beaker, 100 ml of DI water were added. The first $Mg(NO_3)_2$ solution in the first beaker was added dropwise, using a pipette, to the second beaker containing only DI water to form a second $Mg(NO_3)_2$ solution. A magnetic stirrer was placed inside the second beaker and the stirrer was set to stir the second $Mg(NO_3)_2$ solution at a rate of 600 rotations per minute (rpm). While stirring the second $Mg(NO_3)_2$ vigorously at 600 rpm, ammonium hydroxide (NaOH) was added dropwise to the second $Mg(NO_3)_2$ solution. The pH of the resulting solution was maintained in a range of 11 to 12. After adding the ammonium hydroxide, the solution was vigorously stirred at 600 rpm for 60 minutes, during which time, MgO precipitated out of the solution as a white solid. The resulting slurry was then centrifuged and the liquids decanted off. The white solid MgO catalyst was washed 4-5 times with DI water and then dried in a drying oven overnight at 80° C. The MgO catalyst was then calcined according to the same procedure previously described in Example 1.

Example 3: Preparation of MgO: Hydrated Commercial

The MgO isomerization catalyst, the MgO was produced using a hydration method in which MgO is converted to $Mg(OH)_2$ and then calcined to convert the $Mg(OH)_2$ back into MgO. This hydration method may be used to enhance the properties of the MgO isomerization catalyst. MgO was obtained from Sigma Aldrich (Lot #MKBQ2256V, ≥99% trace metals basis). 24.00 g of the MgO was weighed out and added to a 500 mL round-bottom flask. 300 mL of water was added to the MgO and the solution was vigorously shaken for 5 minutes to hydrate the MgO to $Mg(OH)_2$. The round-bottom flask was placed in a water bath maintained at a temperature of from 80° C. to 95° C. and connected to rotary evaporator apparatus. The rotary evaporator was run at 171 rpm, under vacuum of 295 millibar, and while maintaining a coolant at 6° F. The rotary evaporator was run for 3 hours to evaporate all of the water. The flask was placed in a drying oven, which operated between 80° C. and 100° C., overnight. The resulting solid was then calcined using the same calcination procedure described in Example 1 to produce the MgO isomerization catalyst from the $Mg(OH)_2$.

Example 4: Preparation of the Metathesis Catalyst (Mesoporous Silica Catalyst Support Impregnated with Tungsten Oxide)

In a typical preparation, the mesoporous silica catalyst support was first prepared by placing a quantity of a commercially available mesoporous silica, such as Q-10 from Fuji Sylysia (average pore diameter of 10 nm, average relative pore volume of 1.00 ml/g, and an average surface area of 300 $m^2$/g), in a ceramic plate and calcining the mesoporous silica at 200° C. for three hours and then at 575° C. for an additional 5 hours, with a ramping rate of 3° C. per minute to obtain a mesoporous silica catalyst support.

Figure 3:
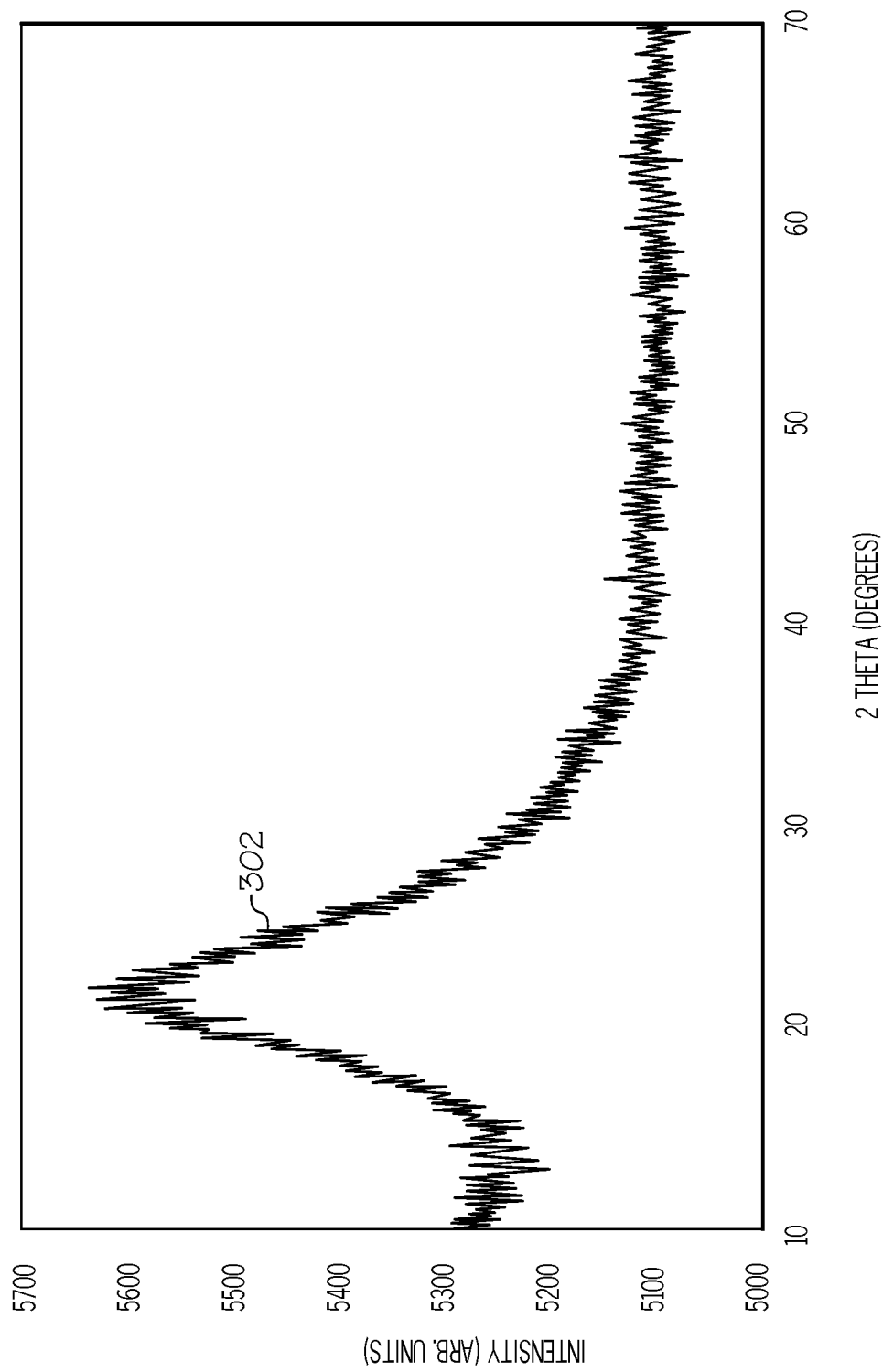
FIG. 3 is an XRD graph illustrating the XRD profile of a mesoporous silica catalyst support, in accordance with one or more embodiments of the present disclosure.

The XRD profile of the mesoporous silica catalyst support of Example 4, before impregnating the mesoporous silica catalyst support with tungsten oxide, is provided in FIG. 3. The broad peak 302 extending from 2θ=15° to 2θ=30° represents the mesoporous silica catalyst support.

To impregnate the mesoporous silica catalyst support with tungsten oxide to synthesize the metathesis catalyst, 2 grams of the mesoporous silica catalyst support were placed in an 80 ml beaker. 0.235 grams of ammonium metatungatate hydrate [$(NH_4)6H_2W_{12}O_{40} \cdot xH_2O$] (99.99% trace metals basis) was mixed with 2 ml of DI water. The ammonium metatungstate hydrate solution was then added drop-wise to the 2 grams of mesoporous silica catalyst support. Typically, 5 drops were placed on the mesoporous silica catalyst support. A glass rod was used to thoroughly mix the mesoporous silica catalyst support and the ammonium metatungstate hydrate solution. Subsequently, the silica catalyst support mixed with the ammonium metatungstate hydrate solution was placed in a drying oven overnight at 80° C. The dried silica catalyst support mixed with the ammonium metatungate hydrate was calcined in a calcination oven at 250° C. for 2 hours, with a ramping rate of 1° C. per minute, and then calcined at 550° C. for 8 hours, with a ramping rate of 3° C. per min until 550° C. was reached. This forms the mesoporous silica catalyst support impregnated with tungsten oxide ($WO_3/SiO_2$).

Figure 4:
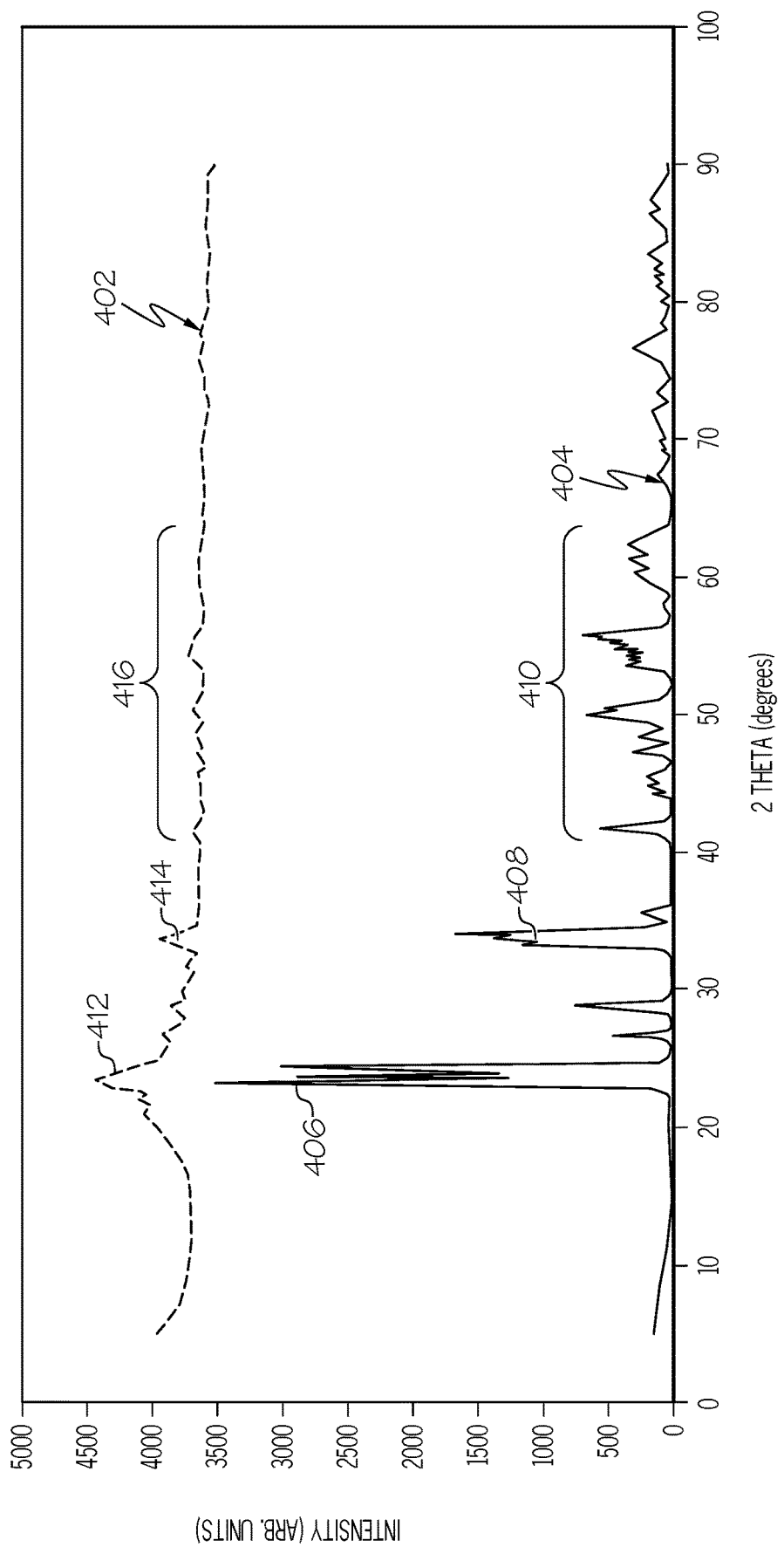
FIG. 4 is an XRD graph illustrating the XRD profile of a mesoporous silica catalyst support impregnated with tungsten oxide, in accordance with one or more embodiments of the present disclosure.

The XRD pattern 402 of the $WO_3/SiO_2$ catalyst of Example 4 is shown in FIG. 4. For comparison, FIG. 4 also includes the XRD pattern 404 for the ammonium metatungstate hydrate after calcining the ammonium metatungstate hydrate at 550° C. to form tungsten oxide. The XRD pattern 404 for the tungsten oxide by itself exhibits a substantial peak 406 between 2θ=22° and 2θ=25°, a smaller peak 408 at 2θ=34°, and several smaller peaks 410 between 2θ=40 and 2θ=65. These peaks are present in the XRD pattern 402 for the $WO_3/SiO_2$ catalyst of example 4 as peaks 412 and 414 and the grouping of peaks 416 between 2θ=40° and 2θ=65°, thus, confirming the impregnation of the tungsten oxide onto the mesoporous silica catalyst support to form the $WO_3/SiO_2$ catalyst.

Example 5: Preparation of Silicalite-1 Cracking Catalyst

In a typical synthesis, 4.26 grams tetrapropylammonium bromide (TPABr) and 0.7407 grams ammonium fluoride ($NH_4F$) were dissolved in 72 ml of DI water and stirred well for 15 minutes. Then, 12 grams of fumed silica ($SiO_2$) were added and stirred well until homogenized. The obtained gel was autoclaved and kept at 200° C. for 2 days. The molar composition of the gel was 1 $SiO_2$: 0.08 TPABr: 0.10 $NH_4F$: 20 $H_2O$. The solid products obtained were washed with water and dried at 80° C. overnight. The template was removed by calcination in air at 750° C. for 5 hours at a ramping rate of 3° C. per min.

Example 6: Preparation of MFI-2000 Cracking Catalyst

In a typical synthesis, 8.52 grams of TPABr and 1.48 grams of $NH_4F$ were dissolved in 150 ml of DI water, and the resulting TPABr solution was stirred well for 20 minutes. 24 grams fumed silica and 0.15 grams of aluminum nitrate were gradually added simultaneously to the TPABr solution while stirring vigorously. Once the solution gelled, the gel was mixed vigorously with a spatula for approximately 10 minutes until homogenized. The obtained gel was autoclaved and kept at 200° C. for 2 days. After two days the autoclave was removed from the oven and quenched in cold water for 30 minutes. The molar composition of gel was 1 $SiO_2$: 0.0005 $Al_2O_3$: 0.08 (TPA)Br: 0.10 $NH_4F$: 20 $H_2O$. The solid products obtained were removed from the autoclave, filtered, washed with 1 liter of DI water, and dried at 80° C. overnight. The solid products were removed from the drying over and calcined at 750° C. for 6 hours with a ramp up of 4° C. per min, producing the MFI-2000 cracking catalyst.

Catalyst Properties

Table 1 includes the mechanical properties of the catalysts prepared in Examples 1 and 4. As indicated in Table 1, the surface area and relative pore volume for the mesoporous silica catalyst support decreases when the mesoporous silica catalyst support is impregnated with the tungsten oxide.

TABLE 1

BET Surface Areas and Relative Pore Volumes of the Isomerization Catalyst of Example 1, the Metathesis Catalysts of Example 4, and the Cracking Catalyst of Example 6

| Catalysts/Supports | BET Surface Area ($m^2/g$) | Relative Pore Volume ($cm^3/g$) |
|---|---|---|
| MgO (Example 1) | 81.94 | 1.786 |
| 100% $SiO_2$ Catalyst Support (Example 4) | 304 | 1.13 |
| Mesoporous $SiO_2$ catalyst support w/$WO_3$ (Example 4) | 274 | 0.81 |
| MFI-2000 Cracking Catalyst (Example 6) | 367 | 0.19 |

Catalyst Evaluation

The prepared catalysts from Examples 1-6 were tested, individually and in various combinations and configurations, for their activity and selectivity for converting 2-butene to propene in a fixed-bed continuous flow reactor (ID 0.25 inches (in), Autoclave Engineers Ltd.) at atmospheric pressure. Fixed amounts of each catalyst—isomerization catalyst (MgO from Example 1), the metathesis catalyst (mesoporous silica catalyst impregnated with tungsten oxide from Example 4), and the cracking catalyst (MFI-2000 from Example 6)—were packed into the reactor tube with grade 20 silicon carbide at the bottom of the reactor. The grade 20 silicon carbide is chemically inert and makes no contribution to the reaction chemistry. Each catalyst type was separated from each adjacent catalyst by quartz wool. Additional layers of quartz wool were placed between the catalyst and the silicon carbide and at the inlet and outlet ends of the reactor.

The catalysts were pretreated and activated under $N_2$ at 550° C. and a flow of 25 standard cubic centimeters per minute (sccm) for 1 hour. All reactions were carried out at three temperatures: 500° C., 525° C., and 550° C. All reactions were carried out at atmospheric pressure at a gas hourly space velocity (GHSV) of 900 $h^{-1}$ and using a feed stream that included 2-butene (5 milliliters/minute (ml/min)) with nitrogen as diluent (25 ml/min). For each reaction at each reaction temperature, the reactor was maintained at the reaction temperature for 3.5 hours.

Examples 7-9: Metathesis Catalyst in a Single Catalyst System

The mesoporous silica catalyst support impregnated with tungsten oxide ($WO_3/SiO_2$) of Example 4 (metathesis catalyst) was tested for its activity and selectivity for converting 2-butene to propene in a fixed-bed continuous flow reactor (ID 0.25 in, Autoclave Engineers Ltd.) at atmospheric pressure. The activity and selectivity of the $WO_3/SiO_2$ catalyst were tested in a single catalyst system. A fixed amount of 2 ml of the $WO_3/SiO_2$ catalyst was packed into the reactor tube with grade 20 silicon carbide positioned downstream of the $WO_3/SiO_2$ catalyst and quartz wool placed between the $WO_3/SiO_2$ catalyst and the silicon carbide and at the inlet and outlet ends of the reactor.

The $WO_3/SiO_2$ catalyst in the reactor system was pretreated and activated under $N_2$ at 550° C. and a flow of 25 sccm for 1 hour. All reactions were carried out at three temperatures: 500° C., 525° C., and 550° C. All reactions were carried out at atmospheric pressure at a GHSV of 900 $h^{-1}$ and using a feed stream that included 2-butene (5 ml/min) with nitrogen as diluent (25 ml/min). For each temperature, the reactor was maintained at the reaction temperature for 3.5 hours. Quantitative analysis of the reaction products for each experiment was performed using an Agilent gas chromatograph with flame ionization detector (FID) (Agilent GC-7890B), equipped with an HP-Al/KCL (50 m×0.53 mm×15 microns) column.

Table 2 summarizes the yields and conversions obtained by the $WO_3/SiO_2$ catalyst in the single catalyst system at each of the reaction temperatures. In Table 2, the values of the yields and conversions of the 2-butene feed were calculated based on an average of values obtained from 5 injections into the gas chromatograph at each temperature once the reaction run was stable. As shown in Table 2, increasing the reaction temperature increased the propene yield. The maximum propene yield was attained at 550° C.

$C_6$+ production given the increased propene output. Running the reactor at 500° C. may potentially provide the benefit of an increased lifetime of the catalyst bed associated with a lower operating temperature

Examples 10-11: Cracking Catalyst in a Single Catalyst System

The cracking catalyst of Example 6 was tested for its activity and selectivity for converting 2-butene to propene in a fixed-bed continuous flow reactor (ID 0.25 in, Autoclave Engineers Ltd.) at atmospheric pressure. The activity and selectivity of the cracking catalyst of Example 6 were tested in a single catalyst system. A fixed amount of 2 ml of the cracking catalyst of Example 6 was packed into the reactor tube with grade 20 silicon carbide positioned downstream of the catalyst and quartz wool placed between the catalyst and the silicon carbide and at the inlet and outlet ends of the reactor.

The cracking catalyst in the reactor system was pretreated and activated under $N_2$ at 550° C. and a flow of 25 sccm for 1 hour. All reactions were carried out at two temperatures: 500° C. and 550° C. All reactions were carried out at atmospheric pressure at a GHSV of 900 $h^{-1}$ and using a feed stream that included 2-butene (5 ml/min) with nitrogen as diluent (25 ml/min). For each reaction temperature, the reactor was maintained at the reaction temperature for 3.5 hours. Quantitative analysis of the reaction products for each experiment was performed using the Agilent gas chromatograph previously described in this disclosure in Examples 7-9.

Table 3 summarizes the yields and conversions obtained by the cracking catalyst of Example 6 in the single catalyst system at each of the reaction temperatures. The cracking

TABLE 2

Performance of the $WO_3/SiO_2$ Metathesis Catalyst in the Single Catalyst System of Examples 7-9

| T | Ethylene (mol %) | Propene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| | | | | Sample = $WO_3/SiO_2$ catalyst | | | | | |
| 500° C. | 1.60 | 18.81 | 22.73 | 13.90 | 0.42 | 16.77 | 20.21 | 5.56 | 60.50 |
| 525° C. | 2.58 | 23.53 | 17.88 | 10.48 | 0.29 | 13.25 | 22.28 | 9.70 | 68.86 |
| 550° C. | 3.41 | 25.48 | 16.02 | 10.71 | 0.38 | 12.01 | 21.59 | 10.12 | 71.97 |

Table 2 demonstrates the increasing trend in the yield of desirable propene formation with temperature increases. Conversely, an increasing trend in the yield of less desirable $C_6$+ hydrocarbons is also observed with temperature increases. As such, running the reactor at 550° C. may provide an increased propene production with an acceptable catalyst of Example 6 was screened for cracking activity as well as any propene production contribution. In Table 3, the values of the yields and conversions of the 2-butene feed were calculated based on an average of values obtained from 5 injections into the gas chromatograph at each temperature once the reaction run was stable.

TABLE 3

Performance of the Cracking Catalyst in the Single Catalyst System of Examples 10-11

| Temp. | Ethylene (mol %) | Propene (mol %) | Trans-Butene (mol %) | 1-Butene (mol %) | Iso-Butene (mol %) | Cis-Butene (mol %) | C5 (mol %) | C6+ (mol %) | Conversion (%) |
|---|---|---|---|---|---|---|---|---|---|
| | | | | | Sample = ZSM-5 | | | | |
| 500° C. | 14.343 | 37.773 | 5.865 | 3.925 | 9.867 | 4.284 | 6.946 | 7.401 | 89.852 |
| 550° C. | 17.534 | 41.771 | 5.563 | 4.135 | 8.945 | 4.137 | 4.023 | 6.746 | 90.300 |

As shown in Table 3, increasing the reaction temperature from 500° C. to 550° C. results in more propene being formed and more $C_5$ and $C_6+$ compounds being cracked. The maximum propene yield is 41.77 percent (%), which was obtained at a reaction temperature of 550° C. Table 3 demonstrates the increasing trend in the yield of desirable propene formation with temperature increases. Similarly, a decreasing trend in the yield of less desirable $C_6+$ hydrocarbons is also observed with temperature increases. As such, running the reactor at 550° C. may provide the desirable benefit of an increased propene production. Without being bound by theory, it is believed that the increase in temperature from 500° C. to 550° C. increases the rate of the cracking reaction, which in turn increases the amount of $C_5$ and $C_6+$ compounds cracked by the cracking catalyst into ethylene and propene at the higher temperature of 550° C.

Examples 12-14: Isomerization Catalyst in a Single Catalyst System

The isomerization catalyst of Example 1 was tested for its activity and selectivity for converting 2-butene to 1-butene and propene in a fixed-bed continuous flow reactor (ID 0.25 in, Autoclave Engineers Ltd.) at atmospheric pressure. The activity and selectivity of the isomerization catalyst of Example 1 were tested in a single catalyst system. A fixed amount of 2 ml of the isomerization catalyst of Example 1 was packed into the reactor tube with grade 20 silicon carbide positioned downstream of the isomerization catalyst and quartz wool placed between the isomerization catalyst and the silicon carbide and at the inlet and outlet ends of the reactor.

The isomerization catalyst in the reactor system was pretreated and activated under $N_2$ at 550° C. and a flow of 25 sccm for 1 hour. All reactions were carried out at three temperatures: 450° C., 500° C., and 550° C. All reactions were carried out at atmospheric pressure at a GHSV of 900 $h^{-1}$ and using a feed stream that included 2-butene (5 ml/min) with nitrogen as diluent (25 ml/min). For each reaction temperature, the reactor was maintained at the reaction temperature for 4 hours. Quantitative analysis of the reaction products for each experiment was performed using the Agilent gas chromatograph previously described in this disclosure in Examples 7-9.

Table 4 summarizes the yields obtained by the isomerization catalyst of Example 1 in the single catalyst system at each of the reaction temperatures. The isomerization catalyst of Example 1 was screened for any propene production contribution. In Table 4, the values of the yields were calculated based on an average of values obtained from 4 to 5 injections into the gas chromatograph at each temperature once the reaction run was stable.

TABLE 4

Performance of the MgO Isomerization Catalyst in the Single Catalyst System of Examples 12-14

| Temperature (° C.) | Trans-2-Butene (mol %) | Cis-2-Butene (mol %) | 1-Butene (mol %) | Propene (mol %) | Pentene (mol %) |
|---|---|---|---|---|---|
| 450 | 42.24 | 31.79 | 28.55 | — | — |
| 500 | 41.35 | 30.11 | 26.74 | 1 | 0.56 |
| 550 | 40.23 | 30.25 | 27.95 | 1 | 1 |

For comparison, the reactor system was run blank with no catalyst in the reactor. Instead, the reactor was filled with silicon carbide. The reactor was run at three temperatures: 450° C., 500° C., and 550° C. The blank reactor runs at each temperature were carried out at atmospheric pressure at a GHSV of 900 $h^{-1}$ and using a feed stream that included 2-butene (5 ml/min) with nitrogen as diluent (25 ml/min). The reactor was maintained at each temperature for 4 hours. Quantitative analysis of the reaction products for each experiment was performed using the Agilent gas chromatograph previously described in this disclosure in Examples 7-9. Table 5 summarizes the results of the blank runs at each of the reaction temperatures. In Table 5, the values of the yields were calculated based on an average of values obtained from 4 to 5 injections into the gas chromatograph at each temperature once the reactor system was stable.

TABLE 5

Outlet Composition of the Comparative Example of a Blank Reactor Run with No Catalyst in the Reactor

| Temperature (° C.) | Trans-2-Butene (mol %) | Cis-2-Butene (mol %) | 1-Butene (mol %) | Propene (mol %) | Pentene (mol %) |
|---|---|---|---|---|---|
| 450 | 47.21 | 50.00 | 2.79 | — | — |
| 500 | 47.80 | 50.00 | 2.20 | — | — |
| 550 | 47.00 | 50.00 | 3.00 | — | — |

As shown in Table 4, the isomerization catalyst of Example 1 converted approximately one third of the total 2-butenes to 1 butene. Additionally, the isomerization catalyst of Example 1 converted a greater amount of the cis-2-butene to 1-butene compared to the amount of trans-2-butene converted to 1-butene. Table 5 shows the composition of the outlet stream for the reactor was run without the isomerization catalyst or any other catalyst. Comparison of the results of Table 4 with the results of Table 5 indicates that the isomerization catalyst of Example 1 may be effective in converting 2-butenes in a feed stream to 1-butene to maintain a favorable ratio of 2-butenes to 1-butenes in the isomerization reaction product stream, which may enhance downstream conversion of the butenes to propene and ethylene.

Tables 2-4 provide the yield and conversion for each of the metathesis, cracking, and isomerization catalysts evaluated separately as single catalyst systems in Examples 7-14. Specifically, the metathesis, cracking, and isomerization catalysts were individually tested without being combined with one or more of the other catalyst types. This provided a comparison example of the individual performance of the metathesis and cracking catalysts.

Examples 15-19: Comparative Examples of MgO and $WO_3/SiO_2$ Catalysts in Dual Catalyst Reactor Systems Comparative examples of dual catalyst systems having the MgO isomerization catalyst of Example 1 and the $WO_3/SiO_2$ metathesis catalyst of Example 4 were run and the product stream analyzed to determine conversion, yield, and selectivity of the dual catalyst systems.

In Example 15-17, a dual catalyst system was prepared having a first layer of $WO_3/SiO_2$ metathesis catalyst (1 ml), a layer of MgO catalyst (1 ml) positioned downstream of the first layer of $WO_3/SiO_2$ catalyst, and a second layer of $WO_3/SiO_2$ catalyst (1 ml) positioned downstream of the MgO catalyst. A layer of silicon carbide was positioned in the bottom of the reactor, downstream of the second layer of WO$_3$/SiO$_2$ metathesis catalyst. Quartz wool was positioned upstream of the first layer of WO$_3$/SiO$_2$ metathesis catalyst, between the second layer of WO$_3$/SiO$_2$ catalyst and the silicon carbide, and downstream of the silicon carbide. The WO$_3$/SiO$_2$—MgO—WO$_3$/SiO$_2$ dual catalyst reactor system was run at three reaction temperatures, 450° C., 500° C., and 550° C.

In Example 18, a dual catalyst system was prepared having a layer of MgO (1 ml) and a layer of the WO$_3$/SiO$_2$ metathesis catalyst (2 ml) positioned downstream of the MgO catalyst. A layer of silicon carbide was positioned in the bottom of the reactor, downstream of the of the WO$_3$/SiO$_2$ metathesis catalyst. Quartz wool was positioned upstream MgO catalyst, between the WO$_3$/SiO$_2$ catalyst and the silicon carbide, and downstream of the silicon carbide. The MgO (1 ml)-WO$_3$/SiO$_2$ (2 ml) dual catalyst reactor system, thus prepared, was run at a single reaction temperature of 550° C.

In Example 19, a dual catalyst system was prepared having a layer of WO$_3$/SiO$_2$ metathesis catalyst (2 ml) and a layer of MgO (1 ml) positioned downstream of the WO$_3$/SiO$_2$ metathesis catalyst. A layer of silicon carbide was positioned in the bottom of the reactor, downstream of the MgO catalyst. Quartz wool was positioned upstream of the of WO$_3$/SiO$_2$ metathesis catalyst, between the MgO catalyst and the silicon carbide, and downstream of the silicon carbide. The WO$_3$/SiO$_2$ (2 ml)-MgO (1 ml) dual catalyst reactor system, thus prepared, was run at a reaction temperature of 550° C.

The catalysts of the dual catalyst systems of Examples 15-19 were pretreated and activated under N$_2$ at 550° C. and a flow of 25 sccm for 1 hour. All reactions were carried out at atmospheric pressure at a GHSV of 900 h$^{-1}$ and using a feed stream that included 2-butene (5 ml/min) with nitrogen as diluent (25 ml/min). For each reaction system at each reaction temperature, the reactor was maintained at the reaction temperature for 3.5 hours. Quantitative analysis of the reaction products for each experiment was performed using the Agilent gas chromatograph previously described in Example 7-9.

Table 6 summarizes the yields, conversions and selectivity obtained for each of the dual catalyst reaction systems of comparative Examples 15-19.

TABLE 6

Performance of the Dual Stage Catalyst System of Comparative Example 15-19 Having MgO as the Isomerization Catalyst and WO$_3$/SiO$_2$ as the Metathesis Catalyst

| | Dual Catalyst Comparative Examples | | | | |
|---|---|---|---|---|---|
| Example | 15 | 16 | 17 | 18 | 19 |
| Temperature ° C. | 450 | 500 | 550 | 550 | 500 |
| Yield (mol. %) | | | | | |
| Methane | 0.082 | 0.163 | 1.658 | 2.843 | 0.230 |
| Ethane | 0.000 | 0.085 | 0.856 | 1.081 | 0.085 |
| Ethylene | 2.955 | 4.752 | 7.551 | 9.169 | 1.314 |
| Propane | 0.000 | 0.000 | 0.877 | 0.766 | 0.000 |
| Propene | 23.405 | 27.108 | 31.974 | 33.808 | 18.888 |
| Iso-Butane | 0.000 | 0.000 | 0.000 | 0.000 | 0.000 |
| N-Butane | 0.228 | 0.000 | 0.707 | 0.457 | 0.000 |
| Trans-Butene | 15.844 | 12.606 | 11.275 | 9.928 | 21.039 |
| 1-Butene | 10.781 | 9.388 | 9.315 | 9.180 | 16.994 |
| Iso-Butene | 2.322 | 3.180 | 2.037 | 1.084 | 0.518 |
| Cis-Butene | 11.771 | 9.506 | 8.594 | 7.674 | 15.772 |
| C$_5$ | 19.177 | 18.466 | 12.061 | 11.774 | 20.457 |
| C$_6$+ | 13.643 | 14.745 | 13.096 | 12.226 | 4.703 |
| Total Olefins (C$_3$= & C$_2$=) | 26.360 | 31.861 | 39.524 | 42.977 | 20.202 |
| Conversion (mol. %) | | | | | |
| Conversion | 72.386 | 77.888 | 80.131 | 82.398 | 63.189 |
| Conversion-C$_4$ | 59.283 | 65.320 | 68.779 | 72.125 | 45.677 |
| Selectivity | | | | | |
| Propene Selectivity | 32.322 | 34.804 | 39.904 | 41.030 | 29.881 |
| Ethylene Selectivity | 4.072 | 6.101 | 9.422 | 11.128 | 2.078 |
| Isobutene Selectivity | 3.207 | 4.083 | 2.542 | 1.315 | 0.820 |

As shown in Table 6, the maximum propene yield was 33.808 mol. %, which was obtained using the MgO (1 ml)-WO$_3$/SiO$_2$ (2 ml) reactor configuration of Example 18 at a reaction temperature of 550° C. Thus, the maximum yield in the dual catalyst reactor system was achieved when the MgO was placed in the first layer and the WO$_3$/SiO$_2$ metathesis catalyst was placed in the second layer, downstream of the MgO catalyst. This configuration resulted in the greatest quantity of propene and ethylene produced. As the results for Example 15 demonstrate, when the MgO catalyst is placed downstream of the WO$_3$/SiO$_2$ metathesis catalyst, the metathesis activity may be significantly reduced.

Examples 20-22: Comparative Examples of WO$_3$/SiO$_2$ and Cracking Catalysts in Dual Catalyst Reactor Systems Comparative examples of dual catalyst systems having the WO$_3$/SiO$_2$ metathesis catalyst of Example 4 and the cracking catalyst of Example 6 were run and the product stream analyzed to determine conversion, yield, and selectivity of the dual catalyst systems. This configuration represents the multiple-stage catalyst system of the present disclosure in the absence of the isomerization catalyst (MgO).

For Examples 20-22, a dual catalyst system was prepared having a layer of WO$_3$/SiO$_2$ metathesis catalyst of Example 4 (1 ml) and a layer of the cracking catalyst of Example 6 (1 ml) positioned downstream of the WO$_3$/SiO$_2$ catalyst. A layer of silicon carbide was positioned in the bottom of the reactor, downstream of the cracking catalyst. Quartz wool was positioned upstream of the WO$_3$/SiO$_2$ metathesis catalyst, between the cracking catalyst and the silicon carbide, and downstream of the silicon carbide. The WO$_3$/SiO$_2$-cracking catalyst dual catalyst reactor system was run at three reaction temperatures: 450° C., 500° C., and 550° C.

The catalysts in the dual catalyst system were pretreated and activated under N$_2$ at 550° C. and a flow of 25 sccm for 1 hour. All reactions were carried out at atmospheric pressure at a GHSV of 900 h−1 and using a feed stream that included 2-butene (5 ml/min) with nitrogen as diluent (25 ml/min). For each reaction system at each reaction temperature, the reactor was maintained at the reaction temperature for 3.5 hours. Quantitative analysis of the reaction products for each experiment was performed using the Agilent gas chromatograph previously described in Examples 7-9.

Table 7, subsequently discussed in relation to Examples 23-25, summarizes the yields, conversions and selectivities obtained for each of the dual catalyst reaction systems of comparative Examples 20-22. As indicated in Table 7, the maximum yield of propene for the $WO_3/SiO_2$-MFI-2000 dual catalyst reactor system of Examples 20-22 was 43.360 mol. %, which was achieved at a reaction temperature of 550° C.

Examples 23-25: MgO, $WO_3/SiO_2$, and Cracking Catalyst in a Triple Catalyst System Dual catalyst reactor Examples 15-19 indicated that the highest propene yields were achieved when the MgO isomerization catalyst was positioned upstream of the $WO_3/SiO_2$ metathesis catalyst. Accordingly, experiments were performed using a triple catalyst reactor system that includes the MgO isomerization catalyst of Example 1, the $WO_3/SiO_2$ metathesis catalyst of Example 4, and the cracking catalyst of Example 6.

For Examples 23-25, a triple catalyst system was prepared having a layer of MgO isomerization catalyst (1 ml), a layer of $WO_3/SiO_2$ metathesis catalyst (1 ml) positioned downstream of the layer of MgO catalyst, and a layer of the cracking catalyst of Example 6 (1 ml) positioned downstream of the $WO_3/SiO_2$ catalyst. A layer of silicon carbide was positioned in the bottom of the reactor, downstream of the cracking catalyst. Quartz wool was positioned upstream of the MgO catalyst, between each catalyst layer, between the cracking catalyst and the silicon carbide, and downstream of the silicon carbide. The MgO—$WO_3/SiO_2$—cracking catalyst triple catalyst reactor system was run at three reaction temperatures, 450° C., 500° C., and 550° C.

The catalysts were pretreated and activated under $N_2$ at 550° C. and a flow of 25 sccm for 1 hour. All reactions were carried out at atmospheric pressure at a GHSV of 900 $h^{-1}$ and using a feed stream that included 2-butene (5 ml/min) with nitrogen as diluent (25 ml/min). For each reaction system at each reaction temperature, the reactor was maintained at the reaction temperature for 3.5 hours. Quantitative analysis of the reaction products for each experiment was performed using the Agilent gas chromatograph previously described in Examples 7-9.

Table 7 summarizes the yields, conversions and selectivity obtained for the triple catalyst reactor systems of Examples 23-25 at each reaction temperature and compares this data to the yield, conversion and selectivity data obtained for the dual catalyst reactor system of Examples 20-22.

TABLE 7

Performance of the Triple Stage Catalyst System of Example 23-25 Having the MgO Isomerization Catalyst Compared Against Performance of the Dual Stage Catalyst System of Examples 20-22 Having Only the Metathesis Catalyst and the Cracking Catalyst

| | Triple Stage Catalyst System MgO550—$WO_3/SiO_2$ - MFI-2000 | | | Dual Stage Catalyst System $WO_3/SiO_2$ - MFI-2000 | | | % Change | Yield Difference |
|---|---|---|---|---|---|---|---|---|
| Example | 23 | 24 | 25 | 20 | 21 | 22 | Triple vs. Double | |
| Temperature ° C. | 450 | 500 | 550 | 450 | 500 | 550 | 550 | |
| Yield (mol. %) | | | | | | | | |
| Methane | 0.000 | 0.119 | 0.322 | 0.000 | 0.101 | 0.238 | | 0.08 |
| Ethane | 0.000 | 0.124 | 0.194 | 0.074 | 0.102 | 0.151 | | 0.04 |
| Ethylene | 7.515 | 12.298 | 16.090 | 7.107 | 10.391 | 14.489 | 11% | 1.60 |
| Propane | 2.740 | 2.193 | 1.607 | 2.801 | 2.232 | 1.727 | | −0.12 |
| Propene | 33.362 | 40.659 | 44.457 | 33.409 | 38.897 | 43.360 | 2.5% | 1.10 |
| Iso-Butane | 3.746 | 1.765 | 0.792 | 4.101 | 2.324 | 1.131 | | −0.34 |
| N-Butane | 2.199 | 1.283 | 0.777 | 2.430 | 1.710 | 1.039 | | −0.26 |
| Trans-Butene | 7.294 | 6.850 | 6.186 | 7.670 | 7.340 | 7.073 | | −0.89 |
| 1-Butene | 4.541 | 4.815 | 4.851 | 4.117 | 4.402 | 4.579 | | 0.27 |
| Iso-Butene | 13.146 | 11.753 | 10.153 | 13.220 | 12.013 | 10.960 | −0.7% | −0.81 |
| Cis-Butene | 5.220 | 5.040 | 4.632 | 5.371 | 5.250 | 5.119 | | −0.49 |
| $C_5$ | 10.910 | 7.461 | 5.623 | 13.100 | 10.132 | 6.718 | | −1.10 |
| $C_6+$ | 9.326 | 5.640 | 4.315 | 6.637 | 5.126 | 3.418 | | 0.90 |
| Total Olefins ($C_3$= & $C_2$=) | 40.877 | 52.957 | 60.547 | 40.516 | 49.288 | 57.849 | 4.7% | 2.70 |
| Conversion (mol. %) | | | | | | | | |
| Conversion | 87.486 | 88.110 | 89.182 | 86.959 | 87.410 | 87.808 | | 1.37 |
| Conversion-$C_4$ | 69.799 | 71.542 | 74.178 | 69.622 | 70.994 | 72.270 | | 1.91 |
| Selectivity | | | | | | | | |
| Propene Selectivity | 38.134 | 46.146 | 49.849 | 38.420 | 44.301 | 49.279 | 1.2% | 0.57 |
| Ethylene Selectivity | 8.590 | 13.958 | 18.042 | 8.172 | 11.888 | 16.499 | 9.4% | 1.54 |
| Isobutene Selectivity | 15.027 | 13.339 | 11.385 | 15.203 | 13.744 | 12.481 | −8.8% | −1.10 |

Table 7 demonstrates the superior performance of the triple bed catalyst system in accordance with the present disclosure over a comparative dual catalyst system. The triple bed catalyst system included the dual catalyst system (Examples 20-22) with the added MgO isomerization catalyst of Example 1 in an isomerization reaction zone positioned upstream of the $WO_3/SiO_2$ metathesis catalyst. Compared to the dual catalyst system of Examples 20-22, introduction of the MgO isomerization catalyst layer in the triple catalyst system upstream of the metathesis and cracking catalyst layers, as in Examples 23-25, resulted in unexpectedly high yields of propene and ethylene, which increased by 2.5% and 11%, respectively, over the dual catalyst system having only the $WO_3/SiO_2$ and cracking catalysts. Also, the yield of the undesirable isobutene by-product decreased by 0.7% when the MgO was used as the isomerization catalyst. The total olefins yield for the MgO—$WO_3/SiO_2$— cracking triple catalyst system of Example 25 increased by 4.7% over the $WO_3/SiO_2$— cracking dual catalyst system of comparative Example 22. Thus, the data in Table 7 demonstrates that the triple-catalyst system of Examples 23-25, which included the MgO of Example 1 as the isomerization catalyst, performed better with respect to olefin yield and reduction of undesirable by-products than the dual-catalyst systems of Examples 20-22. Introducing the MgO isomerization catalyst layer unexpectedly increased the yields of olefins and decreased the production of undesirable by-products such as isobutene.

Figure 5:
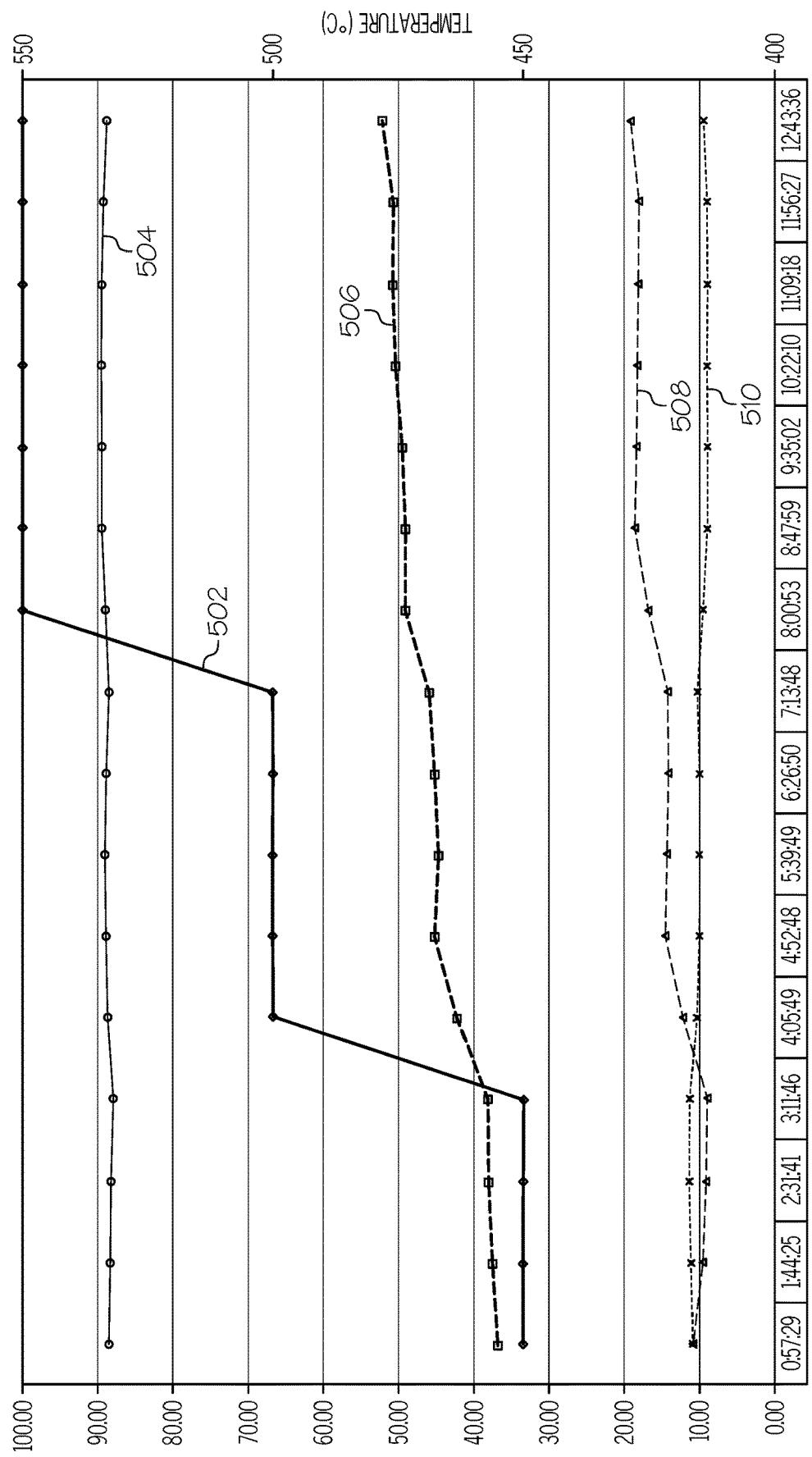
FIG. 5 is a graph illustrating the performance of a multiple-stage catalyst system over time and reaction temperature changes, in accordance with one of more embodiments of the present disclosure.

With reference to FIG. 5, the multiple-stage catalyst system demonstrates a stable conversion and selectivity at various temperatures over a period of time. The triple-catalyst system of Examples 23-25 was utilized for the reaction of 2-butene to propene at reaction temperatures of 450° C., 500° C., and 550° C. at atmospheric pressure with a GHSV of 900 $h^{-1}$. The data of FIG. 5 is also subsequently presented in Table 8. FIG. 5 illustrates the reaction temperature 502 (° C.), overall conversion 504 (%), selectivity of propene 506, selectivity of ethylene 508, and selectivity of isobutene 510 as a function of time-on-stream for the multiple-stage catalyst system. The slope of the overall conversion 504, selectivity of propene 506 and selectivity of ethylene 508 are all steady or increasing throughout the 12 hour run time of the reaction system, which indicates that the multiple-catalyst system may be stable and no deactivation of the downstream catalysts may have occurred.

TABLE 8

Temperature, Conversion, and Selectivity versus On-Stream Time for the Triple-Stage Catalyst System of Examples 23-25
Examples 23-25: Temperature, Conversion, and Selectivity Versus Time On Stream

| On Stream Time (hr:min:sec) | Temperature (° C.) | Overall Conversion (mol %) | Propene Selectivity (%) | Ethylene Selectivity (%) | Isobutene Selectivity (%) |
| --- | --- | --- | --- | --- | --- |
| 0:57:29 | 450 | 88.566 | 36.637 | 10.794 | 13.633 |
| 1:44:35 | 450 | 88.209 | 37.254 | 9.448 | 14.114 |
| 2:31:41 | 450 | 88.038 | 37.677 | 9.170 | 14.355 |
| 3:18:46 | 450 | 87.858 | 37.929 | 8.923 | 14.555 |
| 4:05:49 | 500 | 88.636 | 41.944 | 12.077 | 12.955 |
| 4:52:48 | 500 | 88.789 | 45.038 | 14.366 | 12.562 |
| 5:39:49 | 500 | 88.916 | 44.430 | 14.163 | 12.393 |
| 6:26:50 | 500 | 88.723 | 45.179 | 13.998 | 12.546 |
| 7:13:48 | 500 | 88.403 | 46.005 | 14.089 | 13.043 |
| 8:00:53 | 550 | 88.871 | 48.919 | 16.621 | 12.086 |
| 8:47:59 | 550 | 89.495 | 48.964 | 18.373 | 11.054 |
| 9:35:02 | 550 | 89.476 | 49.501 | 18.353 | 11.129 |
| 10:22:10 | 550 | 89.397 | 49.834 | 18.126 | 11.185 |
| 11:09:18 | 550 | 89.342 | 49.955 | 18.007 | 11.248 |
| 11:56:27 | 550 | 89.252 | 49.893 | 17.927 | 11.363 |
| 12:43:36 | 550 | 88.767 | 52.067 | 19.160 | 11.938 |

Examples 26-28: MgO, $WO_3/SiO_2$, and Cracking Catalyst in a Triple Catalyst System In the following Examples 26-28, the volume of the MgO isomerization catalyst was doubled in the MgO—$WO_3/SiO_2$— cracking triple catalyst reactor system to investigate the effect of changing the volumetric ratio of the MgO to the $WO_3/SiO_2$ catalyst on the performance of the triple catalyst reactor system.

For Examples 26-28, a triple catalyst system was prepared having a layer of MgO isomerization catalyst (2 ml) from Example 1, a layer of $WO_3/SiO_2$ metathesis catalyst (1 ml) from Example 4 positioned downstream of the layer of MgO, and a layer of cracking catalyst (1 ml) from Example 6 positioned downstream of the $WO_3/SiO_2$ catalyst. The volume of the MgO isomerization catalyst was increased to 2 mL as compared to the 1 mL volume of MgO used in Examples 23-25. A layer of silicon carbide was positioned in the bottom of the reactor, downstream of the layer of cracking catalyst. Quartz wool was positioned upstream of the MgO, between each catalyst layer, between the cracking catalyst and the silicon carbide, and downstream of the silicon carbide. The MgO (2 ml)-$WO_3/SiO_2$ (1 ml)-cracking catalyst (1 ml) triple catalyst reactor system was run at three reaction temperatures: 450° C., 500° C., and 550° C.

The catalysts of the triple catalyst reactor system of Examples 26-28 were pretreated and activated under $N_2$ at 550° C. and a flow of 25 sccm for 1 hour. All reactions were carried out at atmospheric pressure at a GHSV of 900 $h^{-1}$ and using a feed stream that included 2-butene (5 ml/min) with nitrogen as diluent (25 ml/min). For each reaction system at each reaction temperature, the reactor was maintained at the reaction temperature for 3.5 hours. Quantitative analysis of the reaction products for each experiment was performed using the Agilent gas chromatograph previously described in Examples 7-9.

Table 9 summarizes the yields, conversions and selectivity obtained for the triple catalyst reactor systems of Examples 26-28 having the increased MgO isomerization catalyst loading of 2 ml. For comparison, Table 9 includes the yield, conversion and selectivity data for the triple catalyst reactor systems of Examples 23-25, which had an MgO isomerization catalyst load of 1 ml.

TABLE 9

Performance of the Triple Stage Catalyst System of Example 26-28 Having
the Increased Loading of the MgO Isomerization Catalyst Compared Against
Performance of the Triple Stage Catalyst System of Examples 23-25

| | 1 ml MgO Catalyst + 1 ml $WO_3/SiO_2$ Catalyst + 1 ml Cracking Catalyst | | | 2 ml MgO Catalyst + 1 ml $WO_3/SiO_2$ Catalyst + 1 ml Cracking Catalyst | | |
|---|---|---|---|---|---|---|
| Example | 23 | 24 | 25 | 26 | 27 | 28 |
| Temperature ° C. | 450 | 500 | 550 | 450 | 500 | 550 |
| | Yield (mol. %) | | | | | |
| Methane | 0.000 | 0.119 | 0.322 | 0.000 | 0.128 | 0.313 |
| Ethane | 0.000 | 0.124 | 0.194 | 0.084 | 0.137 | 0.190 |
| Ethylene | 7.515 | 12.298 | 16.090 | 7.840 | 12.420 | 17.007 |
| Propane | 2.740 | 2.193 | 1.607 | 2.961 | 2.531 | 1.743 |
| Propene | 33.362 | 40.659 | 44.457 | 33.324 | 40.084 | 46.218 |
| Iso-Butane | 3.746 | 1.765 | 0.792 | 4.094 | 2.096 | 0.931 |
| N-Butane | 2.199 | 1.283 | 0.777 | 2.414 | 1.514 | 0.909 |
| Trans-Butene | 7.294 | 6.850 | 6.186 | 7.058 | 6.477 | 6.085 |
| 1-Butene | 4.541 | 4.815 | 4.851 | 4.532 | 4.688 | 4.916 |
| Iso-Butene | 13.146 | 11.753 | 10.153 | 12.787 | 11.131 | 10.049 |
| Cis-Butene | 5.220 | 5.040 | 4.632 | 5.084 | 4.800 | 4.573 |
| C5 | 10.910 | 7.461 | 5.623 | 13.433 | 9.113 | 5.309 |
| C6+ | 9.326 | 5.640 | 4.315 | 6.388 | 4.882 | 4.226 |
| Total Olefins (C3= & C2=) | 40.877 | 52.957 | 60.547 | 41.164 | 52.504 | 63.225 |
| | Conversion (mol. %) | | | | | |
| Conversion | 87.486 | 88.110 | 89.182 | 87.858 | 88.723 | 89.342 |
| Conversion-$C_4$ | 69.799 | 71.542 | 74.178 | 70.538 | 72.904 | 74.377 |
| | Selectivity | | | | | |
| Propene Selectivity | 38.134 | 46.146 | 49.849 | 37.929 | 45.179 | 51.731 |
| Ethylene Selectivity | 8.590 | 13.958 | 18.042 | 8.923 | 13.998 | 22.867 |
| Isobutene Selectivity | 15.027 | 13.339 | 11.385 | 14.555 | 12.546 | 11.248 |

The yields of propene and ethylene were unexpectedly higher when the amount of MgO isomerization catalyst loaded into the reactor was doubled from 1 ml to 2 ml. As shown in Table 7, the propene yield at 550° C. increased by 4% from 44.457 mol. % to 46.218 mol. % when the volumetric ratio of MgO isomerization catalyst to metathesis catalyst to cracking catalyst was increased from 1:1:1 to 2:1:1. Accordingly, doubling the ratio of the MgO isomerization catalyst to metathesis catalyst and cracking catalyst also increased the overall conversion and propene selectivity and decreased isobutene yield for the triple catalyst system. Thus, the data in Table 9 demonstrate that increasing the volumetric ratio of the MgO isomerization catalyst to the metathesis catalyst and to the cracking catalyst may improve the yield, conversion and selectivity performance of the triple catalyst system.

Calculation Methodologies

Determination of "Conversion" was calculated according to formula 1, where $n_i$ is the number of moles of component "i" (2-butenes) entering or leaving the reactor.

$$\text{Conversion} = \frac{n_{i,in} - n_{i,out}}{n_{i,in}} \times 100 \quad (1)$$

Similarly, determination of "Conversion-$C_4$" was calculated according to formula 2.

Conversion-C4=100−(CisButene Yield+TransButene Yield+IsoButene Yield+1-Butene Yield) (2)

Determination of "Selectivity" was calculated according to formula 3.

$$\text{Selectivity} = \frac{\text{Yield of Product}}{\text{Conversion}} \times 100 \quad (3)$$

The surface area of the samples was measured by nitrogen adsorption at 77 Kelvin (K) using AUTOSORB-1 (Quanta Chrome). Before adsorption measurements, samples (ca. 0.1 g) were heated at 220° C. for 2 hours under nitrogen flow. The nitrogen adsorption isotherms of catalysts were measured at liquid nitrogen temperature (77 K). The surface areas were calculated by the Brunauer Emmett-Teller (BET) method. The total relative pore volume was estimated from the amount of $N_2$ adsorbed at P/P0=0.99. Barret E P, Joyner L J, Halenda P H, J. Am. Chem. Soc. 73 (1951) 373-380. The percent improvement, such as the percent change presented in Table 7, is equal to the difference between the improved value and the initial value divided by the initial value. The quotient is then multiplied by 100 to convert the improvement to percent improvement. The initial value could also be a reference value.

A first aspect of the present disclosure may be directed to a process for producing propene, the process comprising at least partially isomerizing butene with an isomerization catalyst to form an isomerization reaction product, the isomerization catalyst comprising magnesium oxide (MgO). The process further comprises at least partially metathesizing the isomerization reaction product with a metathesis catalyst to form a metathesis reaction product, the metathesis catalyst comprising a mesoporous silica catalyst support impregnated with metal oxide. The process further comprises at least partially cracking the metathesis reaction product with a cracking catalyst to form a cracking reaction product, the cracking reaction product comprising propene.

A second aspect of the present disclosure may include the first aspect where the butene is at least partially isomerized in an isomerization reaction zone to form the isomerization reaction product, the isomerization reaction zone comprising the MgO.

A third aspect of the present disclosure may include the first or the second aspect where the isomerization reaction product is at least partially metathesized in a metathesis reaction zone to form the metathesis reaction product, the metathesis reaction zone comprising the mesoporous silica catalyst support impregnated with metal oxide.

A fourth aspect of the present disclosure may include any of the first through third aspects where the metathesis reaction product is at least partially cracked in a cracking reaction zone to form a cracking reaction product, the cracking reaction zone comprising the cracking catalyst.

A fifth aspect of the present disclosure may include the first aspect where the butene is at least partially isomerized in an isomerization reaction zone to form the isomerization reaction product, the isomerization reaction zone comprising the MgO; the isomerization reaction product is at least partially metathesized in a metathesis reaction zone to form the metathesis reaction product, the metathesis reaction zone comprising the mesoporous silica catalyst support impregnated with metal oxide; and the metathesis reaction product is at least partially cracked in a cracking reaction zone to form a cracking reaction product, the cracking reaction zone comprising the cracking catalyst.

A sixth aspect of the present disclosure may include any of the first through fifth aspects where the metathesis reaction zone is downstream of the isomerization reaction zone, and the cracking reaction zone is downstream of the metathesis reaction zone.

A seventh aspect of the present disclosure may include any of the first through sixth aspects where the isomerization reaction zone, metathesis reaction zone, and the cracking reaction zone are disposed within a reactor.

An eighth aspect of the present disclosure may include any of the first through seventh aspects where a volumetric ratio of the MgO in the isomerization reaction zone to the mesoporous silica catalyst support impregnated with metal oxide in the metathesis reaction zone is at least 1:2.

A ninth aspect of the present disclosure may include the first aspect where the butene is at least partially isomerized and at least partially metathesized in a mixed isomerization and metathesis reaction zone to form the metathesis reaction product, the mixed isomerization and metathesis reaction zone comprising the MgO and the mesoporous silica catalyst support impregnated with metal oxide, and the metathesis reaction product is at least partially cracked in a cracking reaction zone downstream of the metathesis reaction zone, the cracking reaction zone comprising the cracking catalyst.

A tenth aspect of the present disclosure may include the first aspect where the butene is at least partially isomerized in an isomerization reaction zone to form an isomerization reaction product, the isomerization reaction zone comprising the MgO, and the isomerization reaction product is at least partially metathesized and at least partially cracked in a mixed metathesis and cracking reaction zone downstream of the isomerization reaction zone, the mixed metathesis and cracking reaction zone comprising the mesoporous silica catalyst support impregnated with metal oxide and the cracking catalyst.

An eleventh aspect of the present disclosure may include any of the first through tenth aspects further comprising introducing an inlet stream to a reaction zone comprising the isomerization catalyst, the inlet stream comprising from 20 weight percent to 60 weight percent of cis- or trans-2-butene, from 10 weight percent to 15 weight percent of 1-butene, and from 15 weight percent to 25 weight percent n-butane.

A twelfth aspect of the present disclosure may include any of the first through eleventh aspects where the isomerization reaction product comprises 1-butene and 2-butene.

A thirteenth aspect of the present disclosure may include any of the first through twelfth aspects where the metathesis reaction product comprises propene and pentene.

A fourteenth aspect of the present disclosure may include any of the first through thirteenth aspects where the cracking reaction product comprises propene.

A fifteenth aspect of the present disclosure may include any of the first through fourteenth aspects where the MgO is pretreated in a calcination process.

A sixteenth aspect of the present disclosure may include the fifteenth aspect where the MgO is calcined at a calcination temperature from 300° C. to 800° C.

A seventeenth aspect of the present disclosure may include any of the first through sixteenth aspects where the metal oxide of the mesoporous silica catalyst support impregnated with metal oxide comprises one or more oxides of molybdenum, oxides of rhenium, and oxides of tungsten.

An eighteenth aspect of the present disclosure may include any of the first through seventeenth aspects where the metal oxide of the mesoporous silica catalyst support impregnated with metal oxide is tungsten oxide ($WO_3$).

A nineteenth aspect of the present disclosure may include the eighteenth aspect where the mesoporous silica catalyst support impregnated with metal oxide comprises from 1 weight percent to 30 weight percent tungsten oxide.

A twentieth aspect of the present disclosure may include the eighteenth aspect where the mesoporous silica catalyst support impregnated with metal oxide comprises from 7 weight percent to 15 weight percent tungsten oxide.

A twenty-first aspect of the present disclosure may include any of the first through twentieth aspects where the mesoporous silica catalyst support impregnated with metal oxide has a surface area of from 200 $m^2/g$ to 600 $m^2/g$.

A twenty-second aspect of the present disclosure may include any of the first through twenty-first aspects where the mesoporous silica catalyst support impregnated with metal oxide has a relative pore volume of at least 0.6 $cm^3/g$.

A twenty-third aspect of the present disclosure may include any of the first through twenty-second aspects where the cracking catalyst is a zeolite catalyst.

A twenty-fourth aspect of the present disclosure may include any of the first through twenty-second aspects where the cracking catalyst is a MFI structured silica-containing catalyst.

A twenty-fifth aspect of the present disclosure may include the twenty-fourth aspect where the MFI structured silica-containing catalyst has a total acidity of from 0.001 mmol/g to 0.5 mmol/g.

A twenty-sixth aspect of the present disclosure may include the twenty-fourth aspect where the MFI structured silica-containing catalyst comprises alumina.

A twenty-seventh aspect of the present disclosure may include the twenty-fourth aspect where the MFI structured silica-containing catalyst is substantially free of alumina.

A twenty-eighth aspect of the present disclosure may be directed to a process for producing propene, the process comprising introducing a stream comprising butene to an isomerization reaction zone comprising an isomerization catalyst, the isomerization catalyst comprising magnesium oxide (MgO); at least partially isomerizing the stream comprising butene in the isomerization reaction zone to form an isomerization reaction product stream; passing the isomerization reaction product stream to a metathesis reaction zone comprising a metathesis catalyst, the metathesis catalyst comprising a mesoporous silica catalyst support impregnated with metal oxide; at least partially metathesizing the isomerization reaction product stream with the metathesis catalyst to form a metathesis reaction product stream; passing the metathesis reaction product stream to a cracking reaction zone comprising a cracking catalyst; and at least partially cracking the metathesis reaction product stream with the cracking catalyst to form a cracking reaction product stream comprising propene.

A twenty-ninth aspect of the present disclosure may include the twenty-eighth aspect where the stream comprising butene comprises from 50 weight percent to 60 weight percent of cis- or trans-2-butene, from 10 weight percent to 15 weight percent of 1-butene, and from 15 weight percent to 25 weight percent n-butane.

A thirtieth aspect of the present disclosure may include the twenty-eighth or twenty-ninth aspects where the metathesis reaction zone is positioned downstream of the isomerization reaction zone.

A thirty-first aspect of the present disclosure may include any of the twenty-eighth through thirtieth aspects where the metathesis reaction zone is positioned downstream of the isomerization reaction zone, and the cracking reaction zone is positioned downstream of the metathesis reaction zone.

A thirty-second aspect of the present disclosure may include any of the twenty-eighth through thirty-first aspects where the volumetric ratio of the MgO to the mesoporous silica catalyst support impregnated with metal oxide is at least 1:2.

A thirty-third aspect of the present disclosure may include any of the twenty-eighth through thirty-second aspects where the MgO is pretreated in a calcination process at a calcination temperature of 400° C. to 600° C. and a ramping rate of from 1° C. per minute to 3° C. per minute.

A thirty-fourth aspect of the present disclosure may include any of the twenty-eighth through thirty-third aspects where the metal oxide of the mesoporous silica catalyst support impregnated with metal oxide comprises tungsten oxide ($WO_3$).

A thirty-fifth aspect of the present disclosure may include any of the twenty-eighth through thirty-fourth aspects where the isomerization reaction, the metathesis reaction, and the cracking reaction are performed at a temperature of from 400° C. to 600° C.

A thirty-sixth aspect of the present disclosure may include any of the twenty-eighth through thirty-fifth aspects where the isomerization reaction product stream comprises 1-butene and 2-butene.

A thirty-seventh aspect of the present disclosure may include any of the twenty-eighth through thirty-sixth aspects where the metathesis reaction product stream comprises propene and pentene.

A thirty-eighth aspect of the present disclosure may be directed to a multiple-stage catalyst system for producing propene, the multiple-stage catalyst system comprising an isomerization reaction zone, a metathesis reaction zone downstream of the isomerization reaction zone, and a cracking reaction zone downstream of the metathesis reaction zone. The isomerization reaction zone comprises magnesium oxide (MgO), the metathesis reaction zone comprises a mesoporous silica catalyst support impregnated with metal oxide, and the cracking reaction zone comprises a zeolite catalyst, where the zeolite catalyst cracks the metathesis product stream to form a cracking product stream comprising propene.

A thirty-ninth aspect of the present disclosure may include the thirty-eighth aspect where the isomerization reaction zone, the metathesis reaction zone, and the cracking reaction zone are disposed in one reactor.

A fortieth aspect of the present disclosure may include the thirty-eighth or the thirty-ninth aspects where a volumetric ratio of the MgO in the isomerization reaction zone to the mesoporous silica catalyst support impregnated with metal oxide in the metathesis reaction zone is at least 1:2.

A forty-first aspect of the present disclosure may include any of the thirty-eighth through fortieth aspects where a volumetric ratio of the MgO in the isomerization reaction zone to the mesoporous silica catalyst support impregnated with metal oxide in the metathesis reaction zone is at least 1:1.

A forty-second aspect of the present disclosure may include any of the thirty-eighth through forty-first aspects where the metal oxide of the mesoporous silica catalyst support impregnated with metal oxide comprises one or more oxides of molybdenum, oxides of rhenium, and oxides of tungsten.

A forty-third aspect of the present disclosure may include any of the thirty-eighth through forty-second aspects where the metal oxide of the mesoporous silica catalyst support impregnated with metal oxide is tungsten oxide ($WO_3$).

A forty-fourth aspect of the present disclosure may include the forty-third aspect where the mesoporous silica catalyst support impregnated with metal oxide comprises from 1 weight percent to 30 weight percent tungsten oxide.

A forty-fifth aspect of the present disclosure may include the forty-third aspect where the mesoporous silica catalyst support impregnated with metal oxide comprises from 7 weight percent to 15 weight percent tungsten oxide.

A forty-sixth aspect of the present disclosure may include any of the thirty-eighth through forty-fifth aspects where the mesoporous silica catalyst support impregnated with metal oxide has a surface area of from 200 $m^2/g$ to 600 $m^2/g$.

A forty-seventh aspect of the present disclosure may include any of the thirty-eighth through forty-sixth aspects where the mesoporous silica catalyst support impregnated with metal oxide has a relative pore volume of at least 0.60 $cm^3/g$.

A forty-eighth aspect of the present disclosure may include any of the thirty-eighth through forty-seventh aspects where the zeolite catalyst is a MFI structured silica-containing catalyst.

A forty-ninth aspect of the present disclosure may include the forty-eighth aspect where the MFI structured silica-containing catalyst comprises alumina.

A fiftieth aspect of the present disclosure may include the forty-eighth aspect where the MFI structured silica catalyst is substantially free of alumina.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a stream or in a reactor should be appreciated as containing, in some embodiments, a mixture of isomers of that constituent. For example, a compositional range specifying butene may include a mixture of various isomers of butene. It should be appreciated that the examples supply compositional ranges for various streams, and that the total amount of isomers of a particular chemical composition can constitute a range.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for producing propene, the process comprising:
    introducing an inlet stream to an isomerization reaction zone comprising an isomerization catalyst, the isomerization catalyst comprising magnesium oxide (MgO) and the inlet stream comprising from 10 weight percent to 60 weight percent of cis- or trans-2-butene and from 10 weight percent to 60 weight percent of 1-butene;
    isomerizing at least a portion of the inlet stream in the isomerization reaction zone to form an isomerization reaction product stream;
    passing the isomerization reaction product stream to a metathesis reaction zone comprising a metathesis catalyst, the metathesis catalyst comprising a mesoporous silica catalyst support impregnated with metal oxide;
    metathesizing at least a portion of the isomerization reaction product stream with the metathesis catalyst to form a metathesis reaction product stream comprising propene and pentene;
    passing the metathesis reaction product stream, including the propene and pentene, to a cracking reaction zone comprising a cracking catalyst; and
    cracking at least a portion of the metathesis reaction product stream comprising the propene and pentene with the cracking catalyst to form a cracking reaction product stream comprising propene;
    where the isomerization reaction zone, the metathesis reaction zone, and the cracking reaction zone are disposed within a single reactor; and
    the isomerization reaction, the metathesis reaction, and the cracking reaction are performed at a temperature of from 550° C. to 600° C.

2. The process of claim 1, where the metathesis reaction zone is positioned downstream of the isomerization reaction zone.

3. The process of claim 1, where the metathesis reaction zone is positioned downstream of the isomerization reaction zone, and the cracking reaction zone is positioned downstream of the metathesis reaction zone.

4. A process for producing propene, the process comprising:
    introducing an inlet stream to an isomerization reaction zone comprising an isomerization catalyst, the isomerization catalyst comprising magnesium oxide (MgO) and the inlet stream comprising from 10 weight percent to 60 weight percent of cis- or trans-2-butene and from 10 weight percent to 60 weight percent of 1-butene;
    isomerizing at least a portion of the inlet stream in the isomerization reaction zone to form an isomerization reaction product;
    metathesizing at least a portion of the isomerization reaction product in a metathesis reaction zone to form a metathesis reaction product, the metathesis reaction zone including a metathesis catalyst comprising a mesoporous silica catalyst support impregnated with metal oxide; and
    cracking at least a portion of the metathesis reaction product in a cracking reaction zone to form a cracking reaction product, the cracking reaction zone including a cracking catalyst and the cracking reaction product comprising propene;
    where the isomerization reaction zone, the metathesis reaction zone, and the cracking reaction zone are disposed within a single reactor;
    where the metathesis reaction zone is downstream of the isomerization reaction zone; and
    where the isomerizing, metathesizing, and cracking are performed at a temperature of from 550° C. to 600° C.

5. The process of claim 4, where the cracking reaction zone is downstream of the metathesis zone.

6. The process of claim 4, where a volumetric ratio of the MgO in the isomerization reaction zone to the mesoporous silica catalyst support impregnated with metal oxide in the metathesis reaction zone is from 1:2 to 3:1.

7. The process of claim 4, where:
    the metathesis reaction zone and the cracking reaction zone are included in a mixed metathesis and cracking reaction zone; and
    the mixed metathesis and cracking reaction zone comprises the mesoporous silica catalyst support impregnated with metal oxide and the cracking catalyst.

8. The process of claim 4, where the inlet stream comprises:
    from 20 weight percent to 60 weight percent of cis- or trans-2-butene;
    from 10 weight percent to 15 weight percent of 1-butene; and
    from 15 weight percent to 25 weight percent n-butane.

9. The process of claim 4, where the metathesis reaction product comprises propene and pentene.

10. The process of claim 4, where the cracking reaction product comprises propene.

11. The process of claim 4, where the MgO is pretreated in a calcination process.

12. The process of claim 11, where the MgO is calcined at a calcination temperature from 300° C. to 800° C.

13. The process of claim 4, where the metal oxide of the mesoporous silica catalyst support impregnated with metal oxide comprises one or more oxides of molybdenum, oxides of rhenium, and oxides of tungsten.

14. The process of claim 4, where the metal oxide of the mesoporous silica catalyst support impregnated with metal oxide is tungsten oxide ($WO_3$).

15. The process of claim 14, where the mesoporous silica catalyst support impregnated with metal oxide comprises from 1 weight percent to 30 weight percent tungsten oxide.

16. The process of claim 4, where the mesoporous silica catalyst support impregnated with metal oxide has a surface area of from 200 $m^2/g$ to 600 $m^2/g$.

17. The process of claim 4, where the mesoporous silica catalyst support impregnated with metal oxide has a relative pore volume of at least 0.6 $cm^3/g$.

18. The process of claim 4, where the cracking catalyst is a zeolite catalyst.

19. The process of claim 4, where the cracking catalyst is a MFI structured silica-containing catalyst.

20. The process of claim 19, where the MFI structured silica-containing catalyst has a total acidity of from 0.001 mmol/g to 0.1 mmol/g.

21. The process of claim 19, where the MFI structured silica-containing catalyst comprises alumina.

22. The process of claim 19, where the MFI structured silica-containing catalyst is substantially free of alumina.

\* \* \* \* \*